US007097975B1

(12) United States Patent
Frederick

(10) Patent No.: US 7,097,975 B1
(45) Date of Patent: Aug. 29, 2006

(54) PCR METHODS FOR THE IDENTIFICATION AND DETECTION OF THE SOYBEAN RUST PATHOGEN *PHAKOPSORA PACHYRHIZI*

(75) Inventor: Reid D. Frederick, Ashburn, VA (US)

(73) Assignee: The United States of America as represented by the Secretary of Agriculture, Washington, DC (US)

( * ) Notice: Subject to any disclaimer, the term of this patent is extended or adjusted under 35 U.S.C. 154(b) by 274 days.

(21) Appl. No.: 09/907,818

(22) Filed: Jul. 19, 2001

(51) Int. Cl.
*C07H 21/04* (2006.01)
*C12Q 1/68* (2006.01)

(52) U.S. Cl. ........................ 435/6; 435/91.2; 536/23.1; 536/24.3; 536/24.32

(58) Field of Classification Search .................... 435/6, 435/91.2; 536/23.1, 24.3, 23.32
See application file for complete search history.

(56) References Cited

U.S. PATENT DOCUMENTS 5,474,796 A * 12/1995 Brennan .................... 427/2.13
5,688,644 A * 11/1997 Lott et al. ...................... 435/6

OTHER PUBLICATIONS

New England Biolabs Catalog. p. 125. 1996-1997.*

Genbank Accession No. AX132480. "Ribozyme therapy for the treatment of proliferative skin and eye diseases." Robbins et al. May 15, 2001.*

Peterson et al. "Sequence comparison of rRNA ITS regions to differentiate the soybean rust species *Phakopsora pachyrhizi* and *P. meibomiae*". Phytopathyology, vol. 88, No. 9, Supplement, pp. S70-71, Meeting Info. Sep. 1998.*

Frederick, R., et al., "Detection and Discrimination of the Soybean Rust Pathogens *Phakopsora pachyrhizi* and *Phakopsora meibomiae* using PCR", (Abstract), Phytopathology, vol. 90, (6), (Supplement), p. 525, 2000.

* cited by examiner

*Primary Examiner*—Jeanine A. Goldberg
(74) *Attorney, Agent, or Firm*—John D. Fado; Evelyn M. Rabin

(57) ABSTRACT

Soybean rust occurs in many countries throughout Asia, Australia, Africa, and South America. The causal agents of soybean rust are two closely related fungi, *Phakopsora pachyrhizi* and *P. meibomiae*, which are differentiated based upon morphological characteristics of the telia. Determination of the nucleotide sequence of the internal transcribed spacer (ITS) region revealed greater than 99%/95% nucleotide sequence similarity among isolates of either *P. pachyrhizi* or *P. meibomiae*, but only 80% sequence similarity between the two species. Utilizing differences within the ITS region, four sets of PCR primers were designed specifically for *P. pachyrhizi*, and two sets of PCR primers were made specific to *P. meibomiae*. Classical and real-time fluorescent PCR assays were developed to identify and differentiate between *P. pachyrhizi* and *P. meibomiae*.

32 Claims, 16 Drawing Sheets

Figure 1A

| | | |
|---|---|---|
| **AU72-1** | ATAAAAAGCT----AAAGAGTGCACTTTATTGTGGCTCAAAACT--AAACTTTTTA-ATAAACCCATTTA | 63 |
| **AU79-1** | ATAAAAAGCT----AAAGAGTGCACTTTATTGTGGCTCAAAACT--AAACTTTTTA-ATAAACCCATTTA | 63 |
| **HW95** | ATAAAAAGCT----AAAGAGTGCACTTTATTGTGGCTCAAAACT--AAACTTTTTA-ATAAACCCATTTA | 63 |
| **HW98** | ATAAAAAGCT----AAAGAGTGCACTTTATTGTGGCTCAAAACT--AAACTTTTTA-ATAAACCCATTTA | 63 |
| **IN73-1** | ATAAAAAGCT----AAAGAGTGCACTTTATTGTGGCTCAAAACT--AAACTTTTTA-ATAAACCCATTTA | 63 |
| **ID72-1** | ATAAAAAGCT----AAAGAGTGCACTTTATTGTGGCTCAAAACT--AAACTTTTTA-ATAAACCCATTTA | 63 |
| **PH77-1** | ATAAAAAGCT----AAAGAGTGCACTTTATTGTGGCTCAAAACT--AAACTTTTTA-ATAAACCCATTTA | 63 |
| **TW72-1** | ATAAAAAGCT----AAAGAGTGCACTTTATTGTGGCTCAAAACT--AAACTTTTTA-ATAAACCCATTTA | 63 |
| **TW80-1** | ATAAAAAGCT----AAAGAGTGCACTTTATTGTGGCTCAAAACT--AAACTTTTTA-ATAAACCCATTTA | 63 |
| **TW80-2** | ATAAAAAGCT----AAAGAGTGCACTTTATTGTGGCTCAAAACT--AAACTTTTTA-ATAAACCCATTTA | 63 |
| **TH** | ATAAAAAGCT----AAAGAGTGCACTTTATTGTGGCTCAAAACT--AAACTTTTTA-ATAAACCCATTTA | 63 |
| **MUT** | ATAAAAAGCT----AAAGAGTGCACTTTATTGTGGCTCAAAACT--AAACTTTTTA-ATAAACCCATTTA | 63 |
| **TM** | ATAAAAAGCT----AAAGAGTGCACTTTATTGTGGCTCAAAACT--AAACTTTTTA-ATAAACCCATTTA | 63 |
| **BZ82-1** | ATAAAAAGCTTAAAAAAGAGTGCACTTAATTGTGGCTCTAAACACAAAACTTTTTATATAAACCCATTTA | 70 |
| **PR** | ATAAAAAGCTTAAAAAAGAGTGCACTTAATTGTGGCTCTAAACACAAAACTTTTTATATAAACCCATTTA | 70 |

| | | |
|---|---|---|
| **AU72-1** | A-TTGGCTCA-TTGATTGAT-AAGATCTTTGGGCAA-TGGTAGCTTTGAAAAAAGCTGCAACCCACCTAT | 129 |
| **AU79-1** | A-TTGGCTCA-TTGATTGAT-AAGATCTTTGGGCAA-TGGTAGCTTTGAAAAAAGCTGCAACCCACCTAT | 129 |
| **HW95** | A-TTGGCTCA-TTGATTGAT-AAGATCTTTGGGCAA-TGGTAGCTTTGAAAAAAGCTGCAACCCACCTAT | 129 |
| **HW98** | A-TTGGCTCA-TTGATTGAT-AAGATCTTTGGGCAA-TGGTAGCTTTGAAAAAAGCTGCAACCCACCTAT | 129 |
| **IN73-1** | A-TTGGCTCA-TTGATTGAT-AAGATCTTTGGGCAA-TGGTAGCTTTGAAAAAAGCTGCAACCCACCTAT | 129 |
| **ID72-1** | A-TTGGCTCA-TTGATTGAT-AAGATCTTTGGGCAA-TGGTAGCTTTGAAAAAAGCTGCAACCCACCTAT | 129 |
| **PH77-1** | A-TTGGCTCA-TTGATTGAT-AAGATCTTTGGGCAA-TGGTAGCTTTGAAAAAAGCTGCAACCCACCTAT | 129 |
| **TW72-1** | A-TTGGCTCA-TTGATTGAT-AAGATCTTTGGGCAA-TGGTAGCTTTGAAAAAAGCTGCAACCCACCTAT | 129 |
| **TW80-1** | A-TTGGCTCA-TTGATTGAT-AAGATCTTTGGGCAA-TGGTAGCTTTGAAAAAAGCTGCAACCCACCTAT | 129 |
| **TW80-2** | A-TTGGCTCA-TTGATTGAT-AAGATCTTTGGGCAA-TGGTAGCTTTGAAAAAAGCTGCAACCCACCTAT | 129 |
| **TH** | A-TTGGCTCA-TTGATTGAT-AAGATCTTTGGGCAA-TGGTAGCTTTGAAAAAAGCTGCAACCCACCTAT | 129 |
| **MUT** | A-TTGGCTCA-TTGATTGAT-AAGATCTTTGGGCAA-TGGTAGCTTTGAAAAAAGCTGCAACCCACCTAT | 129 |
| **TM** | A-TTGGCTCA-TTGATTGAT-AAGATCTTTGGGCAA-TGGTAGCTTTGAAAAAAGCTGCAACCCACCTAT | 129 |
| **BZ82-1** | AACTGGCTCAGCTACTTCATTGAAGTTTTTGGGCAAATCACAGCTTTGAAAAAAGTTGCAAATCATCTAT | 140 |
| **PR** | AACTGGCTCAGCTACTTCATTGAAGTTTTTGGGCAAATCACAGCTTTGAAAAAAGTTGCAAATCATCTAT | 140 |

Figure 1B

```
AU72-1   TA-ATCATAATCTTTTTTTTTTT-A------ACTCAAAGTCAAATAGAATGTTTTATAAATTTAAATATA   191
AU79-1   TA-ATCATAATCTTTTTTTTTTT-A------ACTCAAAGTCAAATAGAATGTTTTATAAATAAAATATA   191
HW95     TA-ATCATAATCTTTTTTTTTTT-A------ACTCAAAGTCAAATAGAATGTTTTATAAATTTAAATATA   191
HW98     TA-ATCATAATCTTTTTTTTTTT-A------ACTCAAAGTCAAATAGAATGTTTTATAAATTTAAATATA   191
IN73-1   TA-ATCATAATCTTTTTTTTTT--A------ACTCAAAGTCAAATAGAATGTTTTATAAATTTAAATATA   190
ID72-1   TA-ATCATAATCTTTTTTTTTTT-A------ACTCAAAGTCAAATAGAATGTTTTATAAATTTAAATATA   191
PH77-1   TA-ATCATAATCTTTTTTTTTTT-A------ACTCAAAGTCAAATAGAATGTTTTATAAATTTAAATATA   191
TW72-1   TA-ATCATAATCTTTTTTTTTTT-A------ACTCAAAGTCAAATAGAATGTTTTATAAATTTAAATATA   191
TW80-1   TA-ATCATAATCTTTTTTTTTTT-A------ACTCAAAGTCAAATAGAATGTTTTATAAATTTAAATATA   191
TW80-2   TA-ATCATAATCTTTTTTTTTTT-A------ACTCAAAGTCAAATAGAATGTTTTATAAATTTAAATATA   191
TH       TA-ATCATAATCTTTTTTTTTTT-A------ACTCAAAGTCAAATAGAATGTTTTATAAATTTAAATATA   191
MUT      TA-ATCATAATCTTTTTTTTTT--A------ACTCAAAGTCAAATAGAATGTTTTATAAATTTAAATATA   190
TM       TA-ATCATAATCTTTTTTTTTTTTA------ACTCAAAGTCAAATAGAATGTTTTATAAATAAAATATA   192
BZ82-1   TATATCATTGTCATTTTTTATTTTATTAAATAACCAAAGTCACAAAGAATGTTTTATAAATTTTAAAAAA   210
PR       TATATCATTGTCATTTTTTATTTTATTAAATAACCAAAGTCACAAAGAATGTTTTATAAATTTTAAAAAA   210

AU72-1   TATATATA   SEQ ID NO:13     199
AU79-1   TATATA--   SEQ ID NO:14     197
HW95     TATATATA   SEQ ID NO:13     199
HW98     TATATATA   SEQ ID NO:13     199
IN73-1   TATATA--   SEQ ID NO:15     196
ID72-1   TATATA--   SEQ ID NO:16     197
PH77-1   TATATA--   SEQ ID NO:16     197
TW72-1   TATATA--   SEQ ID NO:16     197
TW80-1   TATATA--   SEQ ID NO:16     197
TW80-2   TATATA--   SEQ ID NO:16     197
TH       TATATA--   SEQ ID NO:16     197
MU       TATATA--   SEQ ID NO:15     196
TM       TATATATA   SEQ ID NO:17     200
BZ82-1   TATATATA   SEQ ID NO:18     218
PR       TATATATA   SEQ ID NO:18     218
```

Figure 2A

```
AU72-1    GAAATCTTCTCAACATTATTTCTTTTT-TTTAAAGGGAAAT-TGTTGGATTTTGAGTGTTGCTGTTGCTT    68
AU79-1    GAAATCTTCTCAACATTATTTCTTTTT-TTTAAAGGGAAAT-TGTTGGATTTTGAGTGTTGCTGTTGCTT    68
HW95      GAAATCTTCTCAACATTATTTCTTTTT-TTTAAAGGGAAAT-TGTTGGATTTTGAGTGTTGCTGTTGCTT    68
HW98      GAAATCTTCTCAACATTATTTCTTTTT-TTTAAAGGGAAAT-TGTTGGATTTTGAGTGTTGCTGTTGCTT    68
IN73-1    GAAATCTTCTCAACATTATTTCTTTTT-TTTAAAGGGAAAT-TGTTGGATTTTGAGTGTTGCTGTTGCTT    68
ID72-1    GAAATCTTCTCAACATTATTTCTTTTT-TTTAAAGGGAAAT-TGTTGGATTTTGAGTGTTGCTGTTGCTT    68
PH77-1    GAAATCTTCTCAACATTATTTCTTTTT-TTTAAAGGGAAAT-TGTTGGATTTTGAGTGTTGCTGTTGCTT    68
TW72-1    GAAATCTTCTCAACATTATTTCTTTTT-TTTAAAGGGAAAT-TGTTGGATTTTGAGTGTTGCTGTTGCTT    68
TW80-1    GAAATCTTCTCAACATTATTTCTTTTT-TTTAAAGGGAAAT-TGTTGGATTTTGAGTGTTGCTGTTGCTT    68
TW80-2    GAAATCTTCTCAACATTATTTCTTTTT-TTTAAAGGGAAAT-TGTTGGATTTTGAGTGTTGCTGTTGCTT    68
TH        GAAATCTTCTCAACATTATTTCTTTTT-TTTAAAGGGAAAT-TGTTGGATTTTGAGTGTTGCTGTTGCTT    68
MUT       GAAATCTTCTCAACATTATTTCTTTTT-----AAAGGAAAT-TGTTGGATTTTGAGTGTTGCTGTTGCTT    64
TM        GAAATCTTCTCAACATTATTTCTTTTT-TTTAAAGGGAAAT-TGTTGGATTTTGAGTGTTGCTGTTGCTT    68
BZ82-1    GAATTATTCTCAACTCTTTCTTTATTTACTTGAAGAAAAGCATGTTGGATTTTGAGTGCTGCTGTG---T    67
PR        GAATTATTCTCAACTCTTTCTTTATTTACTTGAAGAAAAGCATGTTGGATTTTGAGTGCTGCTGTG---T    67

AU72-1    TTTTT-GCAGCTCACTTTAAATAAATAAATATATATAAGTTTCAGTATATTT---TGATGTAATAATAA-    133
AU79-1    TTTTT-GCAGCTCACTTTAAATAAATAAATATATATAAGTTTCAGTATATTT---TGATGTAATAATAA-    133
HW95      TTTTT-GCAGCTCACTTTAAATAAATAAATATATATAAGTTTCAGTATATTT---TGATGTAATAATAA-    133
HW98      TTTTT-GCAGCTCACTTTAAATAAATAAATATATATAAGTTTCAGTATATTT---TGATGTAATAATAA-    133
IN73-1    TTTTT-GCAGCTCACTTTAAATAAATAAATATATATAAGTTTCAGTATATTT---TGATGTAATAATAA-    133
ID72-1    TTTTTTGCAGCTCACTTTAAATAAATAAATATATATAAGTTTCAGTATATTT---TGATGTAATAATAA-    134
PH77-1    TTTTTTGCAGCTCACTTTAAATAAATAAATATATATAAGTTTCAGTATATTT---TGATGTAATAATAA-    134
TW72-1    TTTTTTGCAGCTCACTTTAAATAAATAAATATATATAAGTTTCAGTATATTT---TGATGTAATAATAA-    134
TW80-1    TTTTTTGCAGCTCACTTTAAATAAATAAATATATATAAGTTTCAGTATATTT---TGATGTAATAATAA-    134
TW80-2    TTTTT-GCAGCTCACTTTAAATAAATAAATATATATAAGTTTCAGTATATTT---TGATGTAATAATAA-    133
TH        TTTTTTGCAGCTCACTTTAAATAAATAAATATATATAAGTTTCAGTATATTT---TGATGTAATAATAA-    134
MUT       TTTTT-GCAGCTCACTTTAAATAAATAAATATATATAAGTTTCAGTATATTT---TGATGTAATAATAA-    129
TM        TTTTT-GCAGCTCACTTTAAATAAATAAATATATATAAGTTTCAGTATATTT---TGATGTAATAATAA-    133
BZ82-1    TTTAATATAGCTCACTTTAAATAAATAGATATATAAATTCTTGTATATATAT--ATGGTGTAATAATAAC    135
PR        TTTAATATAGCTCACTTTAAATAAATAGATATATAAATTCTTGTATATATATATATGGTGTAATAATAAC    137
```

Figure 2B

| | | |
|---|---|---|
| AU72-1 | AATCATTTCATCAAAAAAATAAATATATGTGAGATTTATTATAACATTAATTGAATGTAAATTTTTTTTT | 203 |
| AU79-1 | AATCATTTCATCAAAAAAATAAATATATGTGAGATTTATTATAACATTAATTGAATGTAAATTTTTTTTT | 203 |
| HW95 | AATCATTTCATCAAAAAAATAAATATATGTGAGATTTATTATAACATTAATTGAATGTAAATTTTTTTTT | 203 |
| HW98 | AATCATTTCATCAAAAAAATAAATATATGTGAGATTTATTATAACATTAATTGAATGTAAATTTTTTTTT | 203 |
| IN73-1 | AATCATTTCATCAAAAAAATAAATATATGTGAGATTTATTATAACATTAATTGAATGTAAATTTTTTTTT | 203 |
| ID72-1 | AATCATTTCATCAAAAAAATAAATATATGTGAGATTTATTATAACATTAATTGAATGTAAATTTTTTTTT | 204 |
| PH77-1 | AATCATTTCATCAAAAAAATAAATATATGTGAGATTTATTATAACATTAATTGAATGTAAATTTTTTTTT | 204 |
| TW72-1 | AATCATTTCATCAAAAAAATAAATATATGTGAGATTTATTATAACATTAATTGAATGTAAATTTTTTTTT | 204 |
| TW80-1 | AATCATTTCATCAAAAAAATAAATATATGTGAGATTTATTATAACATTAATTGAATGTAAATTTTTTTTT | 204 |
| TW80-2 | AATCATTTCATCAAAAAAATAAATATATGTGAGATTTATTATAACATTAATTGAATGTAAATTTTTTTTT | 203 |
| TH | AATCATTTCATCAAAAAAATAAATATATGTGAGATTTATTATAACATTAATTGAATGTAAATTTTTTTTT | 204 |
| MUT | AATCATTTCATCAAAAAAATAAATATATGTGAGATTTATTATAACATTAATTGAATGTAA--TTTTTTTT | 197 |
| TM | AATCATTTCATCAAAAAAATAAATATATGTGAGATTTATTATAACATTAATTGAATGTAAATTTTTTTTT | 203 |
| BZ82-1 | AAACATTTCATCATTGATTTATATAAA---GGAATATAT-ATAGTATTAAATTATTATTATTATTAAATT | 201 |
| PR | AAACATTTCATCATTGATTTATATAAA---GGAATATAT-ATAGTATTAAATTATTATTATTATTAAATT | 203 |

| | | | |
|---|---|---|---|
| AU72-1 | -- | SEQ ID NO:19 | 203 |
| AU79-1 | -- | SEQ ID NO:19 | 203 |
| HW95 | -- | SEQ ID NO:19 | 203 |
| HW98 | -- | SEQ ID NO:19 | 203 |
| IN73-1 | -- | SEQ ID NO:19 | 203 |
| ID72-1 | -- | SEQ ID NO:19 | 204 |
| PH77-1 | TT | SEQ ID NO:20 | 206 |
| TW72-1 | -- | SEQ ID NO:21 | 204 |
| TW80-1 | -- | SEQ ID NO:21 | 204 |
| TW80-2 | T- | SEQ ID NO:22 | 204 |
| TH | -- | SEQ ID NO:21 | 204 |
| MUT | TT | SEQ ID NO:23 | 199 |
| TM | T- | SEQ ID NO:22 | 204 |
| BZ82-1 | TT | SEQ ID NO:24 | 203 |
| PR | TT | SEQ ID NO:25 | 205 |

Figure 3A

```
     |------- ITS5'er ------->
Pme  GGAAGTAAAAGTCGTAACAAGGTTTCCGTAGGTGAACCTGCGGAAGGATCATTAAT   56
Ppa  GGAAGTAAAAGTCGTAACAAGGTTTCCGTAGGTGAACCTGCGGAAGGATCATTAAT   56

Pme  AAAAAGCTTAAAAAAGAGTGCACTTAATTGTGGCTCTAAACACAAAACTTTTTATA  112
Ppa  AAAAAGCT----AAAGAGTGCACTTTATTGTGGCTC--AAAACTAAACTTTTTA-A  105

                                          |------ Pme1'er ------>
Pme  TAAACCCATTTAAACTGGCTCAGCTACTTCATTGA--AGTT-TTTGGCAAATCAC  165
Ppa  TAAACCCATTT-AATTGGCTCA-----TTGATTGATAAGATCTTTGGGC-AATGGT  154
         |------ Ppa3'er ------>          |---- Ppa1'er ---->

Pme  AGCTTTGAAAAAAGTTGCAAATCATCTATTATATCATTGTCATTTTTTATTTTATT  221
Ppa  AGCTTTGAAAAAAGCTGCAACCCACCTATTA-ATCATAATCTTTTTTTTTT-----  204

Pme  AAATAAC-CAAAGTCACAAAGAATGTTTTATAAATTTTAAAAAATATATATAACTT  276
Ppa  ---TAACTCAAAGTCAAATAGAATGTTTTATAAATTTAAATATATATATATAACTT  257

Pme  TTAGCAATGGATCTCTAGGCTCTCATATCGATGAAGAACACAGTGAAATGTGATAA  332
Ppa  TTAACAATGGATCTCTAGGCTCTCATATCGATGAAGAACACAGTGAAATGTGATAA  313

                 |------ Ppm1'er ------>     |---- VIC probe
Pme  TTAATGTGAATTGCAGAATTCAGTGAATCATCAAGTTTTTGAACGCACCTTGTACC  388
Ppa  TTAATGTGAATTGCAGAATTCAGTGAATCATCAAGTTTTTGAACGCACCTTGCACC  369
```

PCR METHODS FOR THE IDENTIFICATION AND DETECTION OF THE SOYBEAN RUST PATHOGEN *PHAKOPSORA PACHYRHIZI*

BACKGROUND OF THE INVENTION

1. Field of the Invention

Soybean rust is caused by two species of fungi, *Phakopsora pachyrhizi* Sydow and *P. meibomiae* (Arthur) Arthur. This invention relates to novel PCR primers and the development of both classical and real-time PCR assays for the rapid detection and discrimination of the soybean rust pathogens *P. pachyrhizi* and *P. meibomiae.*

2. Description of the Relevant Art

Soybean rust is a devastating disease in several soybean growing regions of Asia, Australia, and Africa, and is a potential threat to other countries where soybeans are grown. Soybean rust has been reported in China, Taiwan, Thailand, India, Japan, and Australia in the Eastern Hemisphere and in Brazil, Colombia, Costa Rica, and Puerto Rico in the Western Hemisphere (Asian Vegetable Research and Development Center. 1987. *Bibliography of Soybean Rust,* 1985–1986. AVRDC. Tainan, Taiwan. 103 pages). Yield losses of up to 70–80% have been reported in some fields in Taiwan (Bonde et al. 1976. *Phytopath.* 66:1290–1294; Bromfield, K. R. 1984. *Soybean Rust, Monograph No.* 11. APS Press Inc., St. Paul, Minn., 65 pages). Plants that are heavily infected have fewer pods and smaller seeds that are of poor quality (Bromfield, supra). While soybean rust was found in Hawaii in 1994, it has not yet been observed in the continental U.S. (Sinclair et al. 1996. *Soybean Rust Workshop, Aug.* 9–11, 1995. College of Agricultural, Consumer, and Environmental Sciences, National Soybean Research Laboratory Pub#1, Urbana, Ill., 850 pages).

Soybean rust is caused by two morphologically similar species of *Phakopsora: Phakopsora pachyrhizi* Sydow and *P. meibomiae* (Arthur) Arthur (Ono et al. 1992. *Mycol. Res.* 96: 825–850). *P. pachyrhizi* occurs throughout Australia, Asia, and the islands of Japan, The Philippines, and Taiwan (Ono et al., supra). The soybean rust pathogen recently reported in Hawaii (Sinclair et al., supra) and Zimbabwe (C. Levy, Personal communication) has been tentatively identified as *P. pachyrhizi. P. meibomiae* is found in South and Central America and the Caribbean (Ono et al., supra).

Soybean rust has been identified as a potentially devastating disease if the pathogen were to gain entry and become established in the U.S. Both *P. pachyrhizi* and *P. meibomiae* can infect an unusually broad range of plant species. *P. pachyrhizi* naturally infects 31 species in 17 genera of legumes, and 60 species in 26 other genera have been infected under controlled conditions (Sinclair et al., supra). *P. meibomiae* naturally infects 42 species in 19 genera of legumes, and 18 additional species in 12 other genera have been artificially infected. Twenty-four plant species in 19 genera are hosts for both species (Sinclair et al., supra).

Although both pathogens damage plants, *P. pachyrhizi* is more aggressive and causes considerably more yield loss (Sinclair et al., supra). Previously, isozyme analysis was successful in discriminating between these two *Phakopsora* species (Bonde et al. 1988. *Phytopath.* 78:1491–1494). However, this method is slow and is not useful for detecting and identifying the pathogens in infected plant material. Field identification of soybean rust often is difficult, because symptoms are easily confused with bacterial pustule caused by *Xanthomonas axonopodis* pv. *glycines*, especially during the early stages of disease development (1999. *Compendium of Soybean Diseases,* $4^{th}$ Edition, Hartman et al., Eds. APS Press Inc., St. Paul, Minn., 100 pages; Sinclair et al., supra; Tschanz et al. 1985. In: *Proc. World Soybean Research Conference III*, R. Shibles, Ed. Westview Press, Boulder, Colo., pages 562–567). Even using a hand lens, the lesions of the two diseases on the upper leaf surface look very similar. Likewise, the raised dried blisters of the bacterial pustule lesions on the underside of the leaf appear similar to the uredinial cones of soybean rust (Sinclair et al., supra). Therefore, a molecular-based diagnostic assay that is specific to the soybean rust pathogens, like PCR, would be extremely helpful in making an accurate and timely identification.

The recent findings of soybean rust in Hawaii and Zimbabwe, and the re-emergence of the disease in India, has prompted fears that the pathogen(s) are spreading to new geographic regions. If *P. pachyrhizi* were to gain entry into the continental U.S. and become established, serious losses would likely occur (Yang et al. 1991. *Plant Dis.* 75: 976–982). It has been estimated that yield losses could exceed 10% in most of the U.S., and up to 50% in the Mississippi delta and southeastern states (Sinclair et al.; Yang et al., supra).

Currently, there is no resistance to soybean rust in any of the U.S. commercial soybean cultivars. Some fungicides have been found to be effective against *P. pachyrhizi* by slowing the spread of the pathogen enough so that normal seed set and pod fill can occur (Sinclair et al., supra). However, widespread fungicide applications on soybean fields in the U.S. are not deemed cost effective. As a result, this control option would be useful only for eradication on small acreages. Accurate and timely diagnoses of plant diseases are extremely important so that appropriate control measures and/or eradication procedures can be implemented quickly at an early stage of infection to slow the spread of the pathogen and reduce yield losses. Disease symptoms often aid with making decisions, but a definitive diagnosis requires unambiguous pathogen identification.

There exists a need for new technologies to be examined and novel methods to be developed for the detection and identification of exotic plant pathogens that are deemed significant threats to United States agriculture. Thus, specific primers and methods capable of specifically identifying and differentiating pathogenic *P. pachyrhizi* and *P. meibomiae* isolates are needed.

SUMMARY OF THE INVENTION

We have discovered oligonucleotide sequences which are capable of amplifying DNA fragments specific for identifying the two closely related pathogens when used in a simple and rapid PCR assay. One set of oligonucleotide sequences is specific for identifying *P. pachyrhizi*; another set is useful for selectively and specifically identifying *P. meibomiae.*

In accordance with this discovery, it is an object of the invention to provide the novel oligonucleotides for use as primers for PCR assays for the specific detection and identification of *P. pachyrhizi.*

It is also an object of the invention to provide the novel oligonucleotides for use as primers for PCR assays for the specific detection and identification of *P. meibomiae.*

It is another object of the invention to provide PCR assay methods utilizing the novel primers.

It is an added object of the invention to provide a kit for use in the detection of *P. pachyrhizi.*

It is another added object of the invention to provide a kit for use in the detection of *P. meibomiae.*

Other objects and advantages of the invention will become readily apparent from the following description.

BRIEF DESCRIPTION OF THE DRAWINGS

FIG. 1 shows the nucleotide sequence alignment of the ITS1 region from *P. pachyrhizi* and *P. meibomiae* isolates. Nucleotide differences that occur among either the *P. meibomiae* or *P. pachyrhizi* isolates are denoted with open boxes, whereas differences between the *P. meibomiae* and *P. pachyrhizi* isolates are highlighted with shaded boxes.

FIG. 2 shows the nucleotide sequence alignment of the ITS2 region from *P. pachyrhizi* and *P. meibomiae* isolates. Nucleotide differences that occur among either the *P. meibomiae* or *P. pachyrhizi* isolates are denoted with open boxes, whereas differences between the *P. meibomiae* and *P. pachyrhizi* isolates are highlighted with shaded boxes.

DETAILED DESCRIPTION OF THE INVENTION

Figure 3B:
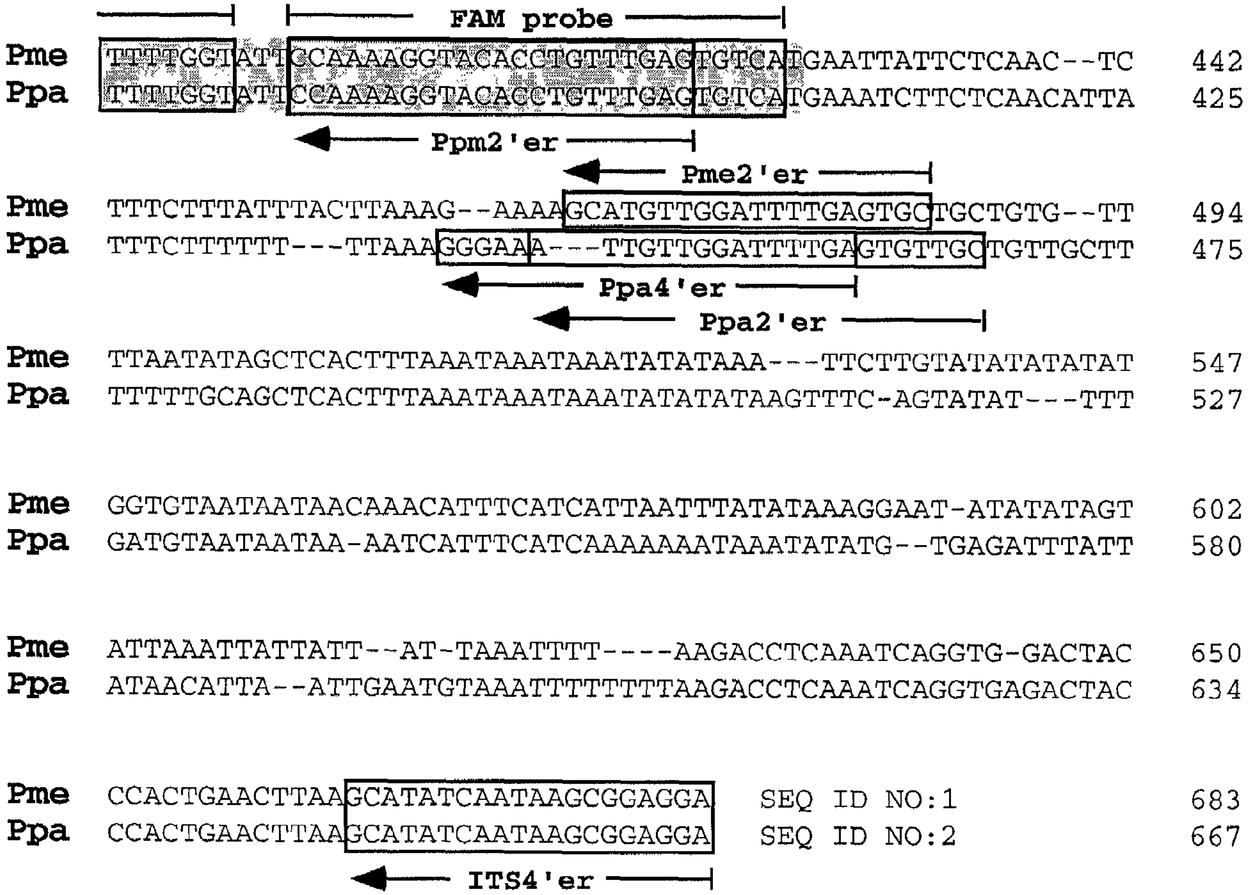
FIG. 3 shows the nucleotide sequence consensus alignment of the ITS1, 5.8S, and ITS2 regions between *P. pachyrhizi* and *P. meibomiae*. The 5.8S rDNA is highlighted with shading. The location of the *P. pachyrhizi*- and *P. meibomiae*-specific PCR primers and VIC®- and FAM-labeled fluorescent probe sequences are delimited by boxes. The nucleotide sequences of *P. meibomiae* (Pme) and *P. pachyrhizi* (Ppa) are identified by SEQ ID NO:1 and SEQ ID NO:2, respectively. The 5' to 3' direction of the PCR primers is shown by arrows. SEQ ID NOs: 3, 5, 7, 9, 11, and 12, representing Ppa1, Ppa3, Pme1, Ppm1, FAM-probe, and VIC®-probe, respectively, appear in FIG. 3 as they are disclosed in the Sequence Listing. Sequences that are disclosed in the Sequence Listing as having SEQ ID NOs: 4, 6, 8, and 10 are complementary to the reverse orientation of the sequences which are identified as Ppa2, Ppa4, Pme2, and Ppm2, respectively, in FIG. 3.
Figure 4:
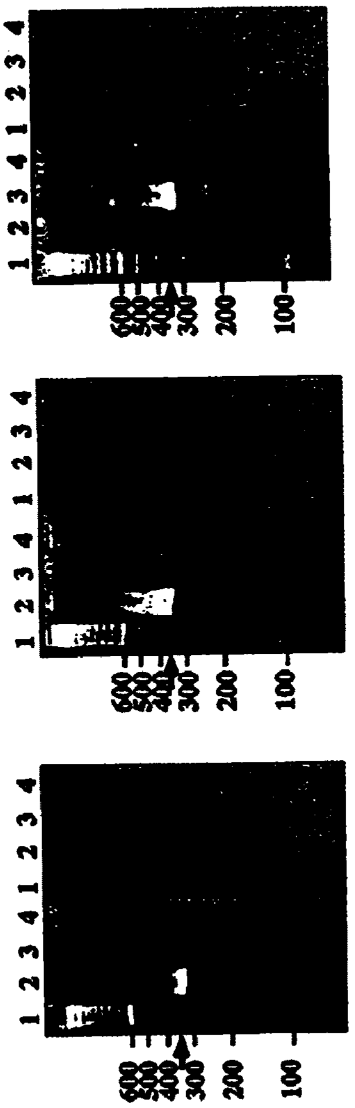
FIG. 4 shows agarose gels (left) and Southern blots (right) of classical PCR assays: the *P. pachyrhizi*-specific assays include the primer sets: Ppa1/Ppa2 (A), Ppa3/Ppa4 (B), Ppm1/Ppa2 (D), and Ppm1/Ppa4 (E); the *P. meibomiae*-specific assays include the primer sets: Pme1/Pme2 (C) and Ppm1/Pme2 (F). The primer combination Ppm1/Ppm2 amplifies a PCR product from both *P. pachyrhizi* and *P. meibomiae* (G). 1=molecular weight markers (100 bp ladder); 2=*P. pachyrhizi* isolate TW72-1; 3=*P. meibomiae* isolate PR; and 4=no DNA template control. PCR products are indicated by arrows. Hybridization probes used were the ITS regions from TW72-1 (A, B, D, E, and G) and BZ82-1 (C and F).
Figure 4:
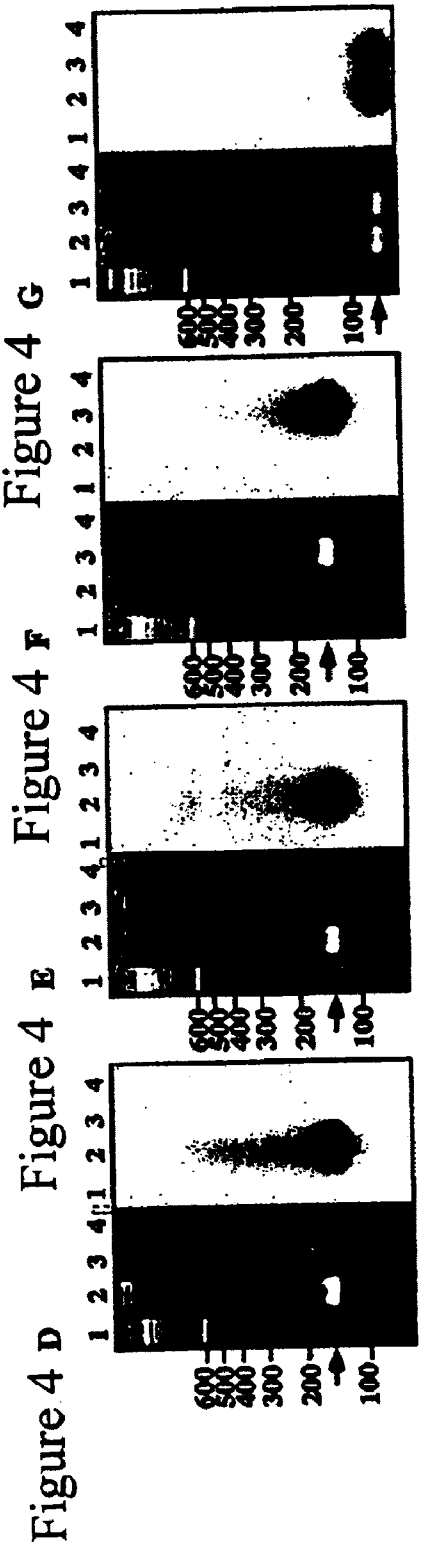

Classical polymerase chain reaction (PCR) methods have been described for the identification and detection of numerous plant pathogens (Henson et al. 1993. *Ann. Rev. Pytopath.* 31: 81–109). Moreover, several real-time fluorescent PCR assays have been developed recently for bacterial (Schaad et al. 1999. *Plant Dis.* 83: 1095–1100), viral (Roberts et al. 2000. *J. Virol. Methods* 88: 1–8; Schoen et al. 1996. *Phytopathology* 86: 993–999), and fungal (Bohm et al. 1999. *J. Phytopathology* 147: 409–416; Frederick et al. 2000. *Phytopathology* 90: 951–960; Zhang et al. 1999. *Phytopathology* 89:796–804) plant pathogens. Real-time PCR has several advantages compared to classical PCR. First, it combines the sensitivity of PCR along with the specificity of nucleic acid hybridization. Second, there is no need for agarose gels and the subsequent Southern blot hybridization steps that are necessary to confirm the identity of PCR products. Third, up to four different fluorescent dyes can be incorporated in a single reaction that allows for multiplexed reactions using different probes for either the same or different pathogens. Finally, many samples can be assayed simultaneously (up to 96 using the ABI Prism 7700 Sequence Detection System), and the assays can be completed within 2–3 hr. Recently, a portable analytical thermal cycling instrument, the Smart Cycler® (Cepheid, Inc., Sunnyvale, Calif.), was introduced for conducting real-time PCR directly in the field (Belgrader et al. 2001. *Anal. Chem.* 73: 286–289; Belgrader et al. 1999. *Science* 284: 449–450). This would negate the requirement for sending samples to the laboratory for analysis, which would result in significantly more rapid diagnoses.

The invention provides for novel PCR assays for the identification and discrimination of the soybean rust pathogens *P. pachyrhizi* and *P. meibomiae*, especially when diagnosticians are presented only with infected plant material. The PCR assays we developed can be used to detect *P. pachyrhizi* from infected plant tissue, with or without urediniospores, and thus to facilitate surveying soybean fields and other plant species that may serve as alternative hosts for either of the *Phakopsora* species. The ability of the PCR assays to differentiate between *P. pachyrhizi* and *P. meibomiae* is attributable to the nucleotide sequence divergence that occurs within the ITS region of these two species. The PCR primers were designed to capitalize on these differences. To further expedite the classical PCR assays, fluorescent probes were developed for use with the *P. pachyrhizi*- and *P. meibomiae*-specific primers in real-time PCR assays. The real-time fluorescent PCR assays are robust, rapid, and allow for high sample throughput (up to 96 samples at one time). Using crude preparations of germinating urediniospores, the *P. pachyrhizi*-specific primers Ppm1/Ppa2 correctly identified 11 out of 11 *P. pachyrhizi* isolates, whereas the *P. meibomiae*-specific primer pair combination Ppm1/Pme2 detected both of the *P. meibomiae* isolates. From infected soybean leaves, an accurate diagnosis can be made in less than 5 hr using the real-time PCR assays. Purified DNA was extracted in less than 2 hr using a commercial DNA extraction kit, and the real-time PCR assays were set-up and performed using an ABI Prism 7700 Sequence Detection System in less than 2.5 hr. No isolation or purification of suspect organisms from infected tissue is necessary, nor is specialized mycological training required in order to perform the real-time PCR assays.

Both the FAM- and VIC®-labeled probes yielded similar levels of fluorescence when use in either of the *Phakopsora* species-specific real-time PCR assays. The VIC® labeled probe and the Ppm1/Ppm2 primers were designed to hybridize to sequences within the 5.8 rDNA so that they could be used to detect the presence of either *Phakopsora* species from any source material. The detection limits of the two *Phakopsora* species-specific assays are similar. The 82 bp PCR product amplified using primers Ppm1 and Ppm2 is highly conserved among a number of different genera of fungi including species of: *Cronartium, Peridermium, Puccinia, Melampsora, Uromyces, Rhizoctonia*, and *Armillaria*. Since the sequence of the VIC® probe and the Ppm2 primer is virtually identical among these species, slight modification to the Ppm1 primer sequence would extend the application of this real-time PCR assay to these other fungi. For example, the last four nucleotides could be removed from at the 3'-end of Ppm1 to create a primer that would match exactly with sequences in these fungi.

We have identified several primers and primer sets as effective for amplifying *P. pachyrhizi* and *P. meibomiae* and to differentiate between them using classical PCR and the TaqMan detection system. The nucleotide sequence of the ITS1 and ITS2 regions of the *P. pachyrhizi* and *P. meibomiae* isolates was determined (FIG. 1 and FIG. 2). These regions were targeted to discriminate between the two species. The ITS1 region ranged in size from 197–200 nucleotides for the *P. pachyrhizi* isolates, and was found to be 218 nucleotides for the *P. meibomiae* isolates. There was greater than 98% sequence identity among the *P. pachyrhizi* isolates using the Bestfit program of the Genetics Computer Group computer package (Version 9.0). No variation was observed between the two *P. meibomiae* isolates. A comparison between the *P. pachyrhizi* and *P. meibomiae* ITS1 regions revealed 49 nucleotide differences or gaps (FIG. 1), representing 22.5% nucleotide sequence divergence between these two *Phakopsora* species.

The ITS2 region ranged in size from 199–206 nucleotides for the *P. pachyrhizi* isolates, and was found to be 203 nucleotides for the *P. meibomiae* isolate BZ82-1 and 205 nucleotides for the *P. meibomiae* isolate PR. There was greater than 95.0% sequence identity among the *P. pachyrhizi* isolates and greater than 99.0% identity between the *P. meibomiae* isolates. A comparison of the *P. pachyrhizi* and *P. meibomiae* ITS2 regions revealed 64 nucleotide differences or gaps (FIG. 2) or approximately 68.5% sequence identity between the species.

A primer is preferably about eighteen to twenty-four nucleotides long. The unique PCR primers Ppa1, Ppa2, Ppa3, Ppa4, Pme1, Pme2, Ppm1, and Ppm2 which encompass the nucleotide differences found in ITS1 (FIG. 1) and ITS2 (FIG. 2) as described above, were derived from sequences within these regions (see FIG. 3) and were used for the rapid identification of *P. pachyrhizi* and *P. meibomiae*. Primers encompassing these and other nucleotide differences in the ITS1 and ITS2 regions as depicted in FIG. 3 can be used in various combinations to identify and differentiate *P. pachyrhizi* and *P. meibomiae*.

Primers can hybridize to a DNA strand with the coding sequence of a target sequence and are designated sense primers. Primers can also hybridize to a DNA strand that is the complement of the coding sequence of a target sequence; such primers are designated anti-sense primers. Primers that hybridize to each strand of DNA in the same location or to one another are known as complements of one another. Primers can also be designed to hybridize to a mRNA sequence complementary to a target DNA sequence and are useful in reverse transcriptase PCR.

The primers can hybridize to a target DNA sequence found in the ITS1 and ITS2 regions of *P. pachyrhizi* and *P. meibomiae*. The primers can preferably hybridize to particular species of *Phakopsora* for which they are specific and not to another species or to microorganisms that mimic their symptoms. The primers can be used in methods and kits for detecting *P. pachyrhizi* and *P. meibomiae* in a biological sample, preferably by detecting amplification products using primers that hybridize to the target sequence. The *P. pachyrhizi*-specific PCR primer sets are: primers Ppa1 (5'-TAAGATCTTTGGGC AATGGT-3'; SEQ ID NO:3)/Ppa2 (5'-GCAACACTCAAAATCCAACAAT-3'; SEQ ID NO:4) and primers Ppa3 (5'-CCCATTTAATTGGCTCATTG-3'; SEQ ID NO:5)/Ppa 4 (5'-TCAAAATCCAACAATTTCCC-3'; SEQ ID NO:6). The primer set comprising the primers Pme1 (5'-GAAGTTTTTGGGCAAATCAC-3'; SEQ ID NO:7)/Pme2 (5'-GCACTC AAAATCCAACATGC-3'; SEQ ID NO:8) specifically recognize *P. meibomiae*. The primer set Ppm1 (5'-GCAGAATTCAGTGAATCATCAAG-3'; SEQ ID NO:9)/Ppm2 (5'-CTCAAACAGGTGTAC-CTTTTGG-3'; SEQ ID NO: 10) recognizes both *P. pachyrhizi* and *P. meibomiae*. The primers of the invention can be used for evaluating and monitoring the efficacy of any treatments utilized to eliminate the pathogenic *P. pachyrhizi* and *P. meibomiae*. The primers of the invention can be used to form probes.

In brief, the DNA amplification products can be detected by (a) providing a biological sample comprising extracted DNA; (b) amplifying a target sequence of the DNA to provide DNA amplification products carrying a selected target DNA sequence; and (c) detecting the presence of *P. pachyrhizi* and *P. meibomiae* by detecting the presence of the DNA amplification products.

The biological sample may be extracted genomic DNA. The biological sample may be a test sample containing DNA extracted from infected plant tissue, with or without urediniospores.

The enzymatic amplification of the DNA sequence is by polymerase chain reaction (PCR), as described in U.S. Pat. No. 4,683,202 to Mullis, herein incorporated by reference. In brief, the DNA sequence is amplified by reaction with at least one oligonucleotide primer or pair of oligonucleotide primers that hybridize to the target sequence or a flanking sequence of the target sequence and a DNA polymerase to extend the primer(s) to amplify the target sequence. The amplification cycle is repeated to increase the concentration of the target DNA sequence. Amplified products are optionally separated by methods such as agarose gel electrophoresis. The amplified products can be detected by either staining with ethidium bromide or by hybridization to a probe sequence. In an alternative embodiment, a probe that hybridizes to the amplified products is labeled either with a biotin moiety and/or at least one probe is labeled with a fluorescently-labeled chromophore. The hybrids are then bound to a solid support such as a bead, multiwell plate, dipstick or the like that is coated with streptavidin. The presence of bound hybrids can be detected using an antibody to the fluorescent tag conjugated to horseradish peroxidase. The enzymatic activity of horseradish peroxidase can be detected with a colored, luminescent or fluorimetric substrate. Conversion of the substrate to product can be used to detect and/or measure the presence of *P. pachyrhizi* and *P. meibomiae* PCR products.

Other methods of PCR using various combination of primers including a single primer to about three primers are known to those of skill in the art and are described in Maniatis (1989. *Molecular Cloning: A Laboratory Manual*. Cold Spring Harbor, N.Y.). Those methods include asymmetric PCR, PCR using mismatched or degenerate primers, reverse transcriptase PCR, arbitrarily primed PCR (Welsh et al. 1990. *Nucleic Acids Res.* 18: 7213–7218), or RAPD PCR, IMS-PCR (Islam et al. 1992. *J. Clin. Micro.* 30: 2801–2806), multiwell PCR (ELOSA) (Luneberg et al. 1993. *J. Clin. Micro.* 31: 1088–1094), and Katz et al. 1993. *Am. J. Vet Res.* 54: 2021–2026). The methods also include amplification using a single primer as described by Judd et al. 1993. *Appl. Env. Microbiol.* 59: 1702–1708).

An oligonucleotide primer sequence must be homologous to a sequence flanking one end of the DNA sequence to be amplified. A pair of oligonucleotide primers, each of which has a different DNA sequence and hybridizes to sequences that flank either end of the target DNA sequence in order for amplification to occur. Design of primers and their characteristics have been described previously. The preferred DNA sequence of the oligonucleotide primer is positive-sense 5'-TAAGATCTTTGGGCAATGGT-3' (Ppa1; SEQ ID NO:3), negative sense 5'-GCAACACTCAAAATCCAA-CAAT-3' (Ppa2; SEQ ID NO:4), positive sense 5'-CCCATT-TAATTGGCTCATTG-3' (Ppa3; SEQ ID NO:5), negative sense 5'-TCAAAATCCAACAATTTCCC-3' (Ppa4; SEQ ID NO:6), positive sense 5'-GAAGTTTTTGGGCAAATCAC-3' (Pme1; SEQ ID NO:7), negative sense 5'-GCACT-CAAAATCCAACATGC-3' (Pme2; SEQ ID NO:8), positive sense 5'-GCAGAA TTCAGTGAATCATCAAG-3' (Ppm1; SEQ ID NO:9), and negative sense 5'-CTCAAACA GGT-GTACCTTTTGG-3' (Ppm2; SEQ ID NO: 10) or complements thereof, or mixtures thereof. The primers may also be degenerate primers that hybridize to the target DNA sequence under hybridization conditions for a primer of that size and sequence complementarity.

The amplified DNA product is optionally separated from the reaction mixture and then analyzed. The amplified gene sequence may be visualized, for example, by electrophoresis in an agarose or polyacrylamide gel or by other like techniques, known and used in the art.

The amplified gene sequence may be directly or indirectly labeled by incorporation of an appropriate visualizing label, as for example, a radioactive, calorimetric, fluorometric or luminescent signal, or the like. In addition, the gel may be stained during or after electrophoresis with a visualizing dye such as ethidium bromide or syber green stain wherein the resulting bands by be visualized under ultraviolet light.

In classical PCR, to conclusively prove the identity of the amplified DNA product, a Southern blot assay should be conducted. The amplified products are separated by electrophoresis on a polyacrylamide or agarose gel, transferred to a membrane such as a nitrocellulose or nylon membrane, and reacted with a labeled oligonucleotide probe. The amplified products may also be detected by reverse blotting hybridization (dot blot) in which an oligonucleotide probe specific to the gene sequence is adhered to a nitrocellulose or polyvinylchloride (PVC) support such as a multi-well plate, and then the sample containing labeled amplified product is added, reacted, washed to remove unbound substance, and a labeled amplified product attached to the probe or the gene sequence imaged by standard methods.

In addition their use in classical PCR assays, the preferred method of amplifying the DNA sequences of *P. pachyrhizi* and *P. meibomiae* is to use the *P. pachyrhizi*-specific and *P. meibomiae*-specific PCR primers with an internal 5'-FAM-labeled oligonucleotide probe sequence in a 5'-fluorogenic real-time TaqMan PCR assay. In most 5'-fluorogenic TaqMan PCR assays, the flanking PCR primers are the same, and the internal fluorescent-labeled probe is designed to be characteristic for a specific sequence (Livak et al. 1995. *PCR Meth. Applic.* 4: 357–362). Since the nucleotide differences within the ITS1 and ITS2 of *P. pachyrhizi* and *P. meibomiae* are randomly scattered, the same probe sequence was used for both *P. pachyrhizi* and *P. meibomiae*; however, different flanking primers were used to provide the specificity to distinguish *P. pachyrhizi* and *P. meibomiae* isolates. For TaqMan PCR, the DNA sequences of the oligonucleotide primer sets include the positive-sense primer Ppm1 5'-GCA-GAATTCAGTGAATCATCAAG-3' (SEQ ID NO:9) together with (1) either of the *P. pachyrhizi*-specific primers: negative sense 5'-GCAACACTCAAAATCCAACAAT-3' (Ppa2; SEQ ID NO:4) or negative sense 5'-TCAAAATC-CAACAATTTCCC-3' (Ppa4; SEQ ID NO:6); (2) the *P. meibomiae*-specific primer: negative sense 5'-GCACT-CAAA ATCCAACATGC-3' (Pme2; SEQ ID NO:8); or (3) the *P. pachyrhizi*- and *P. meibomiae*-specific primer: negative sense 5'-CTCAAACAGGTGTACCTTTTGG-3' (Ppm2; SEQ ID NO: 10) or complements thereof. In addition, other primers of about eighteen to twenty-four nucleotides in length which specifically hybridize to a target region of SEQ ID NO:2, SEQ ID NO:1, or the complement of either, will distinguish between *P. pachyrhizi* and *P. meibomiae* provided that (1) such primers are chosen such that the target region flanked by the primers is such that the amplification products can be detected and quantitated by real-time PCR analysis and (2) at least one of the primers comprises, at its 3' end, at least one of the unique nucleotides in the ITS1 and ITS2 regions identified in FIG. 3 as a mismatch between *P. pachyrhizi* and *P. meibomiae.*

An internal oligonucleotide, a 27-mer probe, was labeled with the chromophore FAM: 5'-FAM-CCAAAAGGTA-CACCTGTTTGAGTGTCA-TAMRA-3' (SEQ ID NO:11). The DNA sequence of the VIC®-labeled probe (SEQ ID NO:12) used with the Ppm1 and Ppm2 primers is shown in Table 2. Additional probes can be made comprising a detectable label conjugated to an oligonucleotide of about twenty to thirty nucleotides that specifically hybridize to a portion of the ITS1/5.8rDNA/ITS2 region.

The TaqMan detection assays offer several advantages over the classical PCR assays developed for *P. pachyrhizi* and *P. meibomiae*. First, the TaqMan assays combine the sensitivity of PCR along with hybridization of the internal oligonucleotide sequence that is present in a *P. pachyrhizi* and *P. meibomiae* sequence. Following PCR, samples do not have to be separated on agarose gels, and the subsequent Southern blots and hybridization steps that are necessary to verify the identity of the PCR products is eliminated. These additional post-PCR confirmation steps can easily add several days for an accurate identification. Using the TaqMan system, the *P. pachyrhizi*- and *P. meibomiae*-specific 5'-fluorogenic assays are completed within 5 hr. Further, the methodology involved in the assay process makes possible the handling of large numbers of samples efficiently and without cross-contamination and is therefore adaptable for robotic sampling. As a result, large numbers of test samples can be processed in a very short period of time using the TaqMan assay. Time is a very important factor when eradication procedures are being considered or when trade issues are involved. Another advantage of the TaqMan system is the potential for multiplexing. Since different fluorescent reporter dyes, as for example FAM and VIC®, can be used to construct probes, several different pathogen systems could be combined in the same PCR reaction, thereby reducing the labor costs that would be incurred if each of the tests were performed individually. The advantages of rapid, conclusive data together with labor and cost efficiency make the TaqMan detection system utilizing the specific primers of the invention a highly beneficial system for monitoring seed pathogens, especially in those circumstances where seed screening results have major commercial and trade consequences.

The primers and amplification method can further be useful for evaluating and monitoring the efficacy of any treatments utilized to control the spread of *P. pachyrhizi* and *P. meibomiae.*

Similarly, the novel primers and methods are very useful for epidemiology and host-pathogen studies as the primers represent a valuable tools for monitoring natural disease spread, tracking specific seedborne bacteria in field studies, and detecting the presence of the fungi in imported seed lots entering *P. pachyrhizi*- and *P. meibomiae*-free areas.

EXAMPLES

The following examples serve as further description of the invention and methods for practicing the invention. They are not intended as being limiting, rather as providing guidelines on how the invention may be practiced.

Example 1

Fungal Isolates and Growth Conditions

The origin and source of *P. pachyrhizi* and *P. meibomiae* isolates used are shown in Table 1. The isolates are maintained at the USDA-ARS Foreign Disease-Weed Science Research Unit (FDWSRU) Plant Pathogen Containment Facility at Ft. Detrick, Md. (Melching et al. 1983. *Plant Dis.* 67: 717–722) under APHIS permit. *P. pachyrhizi* and *P. meibomiae* isolates were propagated by spray inoculation onto the soybean cultivar Williams and red kidney bean, respectively. Red kidney plants were used to propagate *P. meibomiae* isolates because they yield significantly more urediniospores than do soybean plants. Urediniospores were suspended in sterile distilled $H_2O$ containing 0.01% Tween 20 (vol/vol) at a concentration of 2500 spores/ml, and 2.5 ml of inoculum was sprayed per plant onto either soybean or red kidney leaves using an atomizer attached to an air compressor. The plants were incubated overnight (14 to 18 h) in dew chambers at 20° C. and transferred to greenhouses where the temperature ranged from 18 to 30° C. Plants inoculated with different *P. pachyrhizi* and *P. meibomiae* isolates were propagated in separate greenhouses to minimize the chance for cross-contamination. Urediniospores were harvested from infected leaves 10–14 days following inoculation and at subsequent weekly intervals using a mechanical spore harvester (Cherry et al. 1966. *Phytopath.* 56: 1102–1103). Urediniospores were maintained under liquid nitrogen, and frozen spores were heat shocked at 42° C. for five min and hydrated for 12 to 16 hr prior to inoculation.

TABLE 1

| Soybean rust isolates. | | | | |
|---|---|---|---|---|
| Isolate | Origin | Year | Host | Source |
| *P. pachyrhizi* | | | | |
| AU72-1 | Australia | 1972 | soybean | D. E. Bythe, Brisbane |
| AU79-1 | Australia | 1979 | soybean | unknown |
| HW95 | Hawaii | 1995 | soybean | E. Kilgore, Oahu |
| HW98 | Hawaii | 1998 | soybean | E. Kilgore, Oahu |
| IN73-1 | India | 1973 | soybean | D. N. Thapliyal, Pantnagar |
| ID72-1 | Indonesia | 1972 | soybean | unknown |
| PH77-1 | Philippines | 1977 | soybean | Bureau of Plant Industries, Los Banos |
| TW72-1 | Taiwan | 1972 | soybean | Lung-Chi Wu, Taipei |
| TW80-1 | Taiwan | 1980 | soybean | AVRDC, Taiwan |
| TW80-2 | Taiwan | 1980 | soybean | AVRDC, Taiwan |
| TH | Thailand | 1976 | soybean | U. Pupipat, Pak Chang |
| MUT | Zimbabwe | 2000 | soybean | C. Levy, Mutare |
| TM | Zimbabwe | 2000 | soybean | C. Levy, Turk Mine |
| *P. meibomiae* | | | | |
| BZ8201 | Brazil | 1982 | lima beans | J. A. Deslandes |
| PR | Puerto Rico | unknown | several legume spp. & soybean | K. R. Bromfield |

Example 2

DNA Extraction and Recombinant DNA Techniques

For crude DNA preparations, approximately 5 to 10 mg of urediniospores of each isolate were placed onto the surface of sterile distilled $H_2O$ in 50×9 mm petri plates, and the spores were allowed to germinate at room temperature (20–22° C.) overnight. Mycelial mats were collected by filtration onto Whatman No. 1 filter paper, and the tissue was ground in 200 ml of extraction buffer (89 mM Tris-HCl (pH 8.0), 45 mM boric acid, 0.05 mM EDTA, and 1.0% (vol/vol) β-mercaptoethanol) in microcentrifuge tubes using a plastic pestle attached to a power drill. Samples were incubated at 76° C. for 15 min, and then centrifuged at 16,000×g for 10 min to pellet debris. The supernatants were transferred to new tubes and stored at −20° C. as DNA extracts. DNA from the Zimbabwe isolates, MUT and TM, was extracted as described above from intact urediniospores without germination on sterile distilled $H_2O$.

Large scale DNA isolations were conducted using approximately 1.0 g. of urediniospores from either *P. pachyrhizi* isolate TW72-1 or *P. meibomiae* isolate PR. Spores were germinated on sterile distilled $H_2O$, and the mycelial mats were collected as described above and frozen in liquid nitrogen. The frozen samples were ground using acid-washed glass beads in a mortar and pestle. Sixteen ml of grinding buffer (200 mM Tris-HCl (pH 8.0), 250 mM NaCl, 25 mM EDTA, and 0.5% (wt/vol) SDS) were added, and samples were incubated on ice for 5 min. An equal volume of Tris-saturated phenol was added to each sample, and mixed by inverting. Sixteen ml of chloroform:isoamy alcohol (24:1 vol/vol) were added, and the samples were mixed as above. Samples were centrifuged at 10,000×g using a Sorvall (DuPont Instruments) SS-34 rotor for 10 min at 4° C. The aqueous phase was transferred to a new tube, and 1/10 vol of 3 M KOAc (pH 5.5) was added along with 0.6 vol isopropanol. Samples were mixed by inverting and incubated at −20° C. for at least 30 min. The samples were centrifuged at 12,000×g for 20 min as described above, the supernatant was decanted, and the pellets were allowed to air dry. DNA pellets were resuspended and brought to 2.8 ml with TE buffer. Three g of CsCl and 200 ml of ethidium bromide stock solution (10 mg/ml) were added, and the samples were mixed by inverting. The samples were transferred to TL-100 quick-seal tubes (Beckman Instruments, Inc., Palo Alto, Calif.), balanced, and sealed using a heat-sealer (Beckman Instruments, Inc.). The samples were centrifuged at 95,000×g at 15° C. overnight (12 to 16 hr) in a TL 100 tabletop ultracentrifuge (Beckman Instruments, Inc.). Following centrifugation, DNA bands were visualized using a long wavelength ultraviolet light (365 nm, Blak-Ray model UVL-22, Ultra-violet Products Inc., San Gabriel, Calif.). DNA bands were removed using an 18 gauge needle and syringe, and the ethidium bromide and CsCl were extracted as described (1987. *Current Protocols in Molecular Biology*, Ausubel et al., Eds. John Wiley & Sons, New York, N.Y.). The amount of DNA was quantified by spectrophotometry using a SmartSpec 3000 (BioRad Inc., Richmond, Calif.) and confirmed by agarose gel electrophoresis using DNA standards. Purified DNA was stored at −20° C.

DNA was extracted from healthy and infected plant material approximately 10–14 days after inoculation using a Nucleon Phytopure Plant DNA Extraction Kit (Amersham Pharmacia Biotech, Piscataway, N.J.) according to the manufacturer's directions. DNA was extracted from approximately 0.1 g of tissue per sample by pooling 6 leaf disks that were excised from plants using a number 5 cork borer (8 mm diameter).

The ITS regions were cloned from *P. pachyrhizi* and *P. meibomiae* isolates by PCR using the primers ITS4 and ITS5 (White et al. 1990. In: *PCR Protocols*, Innis et al., Eds. Academic Press, San Diego, Calif., pages 315–322). The ITS regions were cloned into the TA cloning vector pCR2.1 (Invitrogen Corp., Carlsbad, Calif.) and transformed into competent *E. coli* INVαF' cells according to the manufacturer's directions. Two clones from two independent PCR amplifications were sequenced for each *Phakopsora* isolate.

Example 3

DNA Sequencing and Analysis

Plasmid DNA was extracted using a Wizard Plasmid Mini-Prep kit (Promega Corp., Madison, Wis.) according to the manufacturer's directions. The concentration of DNA was determined by UV spectrometry at 260 nm using a SmartSpec 3000 (BioRad Inc.), and the DNA was labeled using an ABI Prism Big Dye Terminator Cycle Sequencing Ready Reaction kit (Applied Biosystems, Inc., Foster City, Calif.). The nucleotide sequence was determined by capillary electrophoresis using an ABI Prism 310 Genetic Analyzer (Applied Biosystems, Inc.). Nucleotide sequences were aligned using the Bestfit and Pileup programs of the Genetics Computer Group computer software package (Version 9.0) (Deverex et al. 1984. *Nucleic Acids Res.* 12: 387–395) at the Advanced Biomedical Computing Center of the National Cancer Institute, Frederick, Md.

A nucleotide sequence comparison of the ITS1 (FIG. 1) and ITS2 (FIG. 2) regions of the *P. pachyrhizi* and *P. meibomiae* isolates is shown. The ITS1 region ranged in size from 197–200 nucleotides for the *P. pachyrhizi* isolates, whereas it was found to be 218 nucleotides for the *P. meibomiae* isolates. Among the *P. pachyrhizi* isolates, variation or gaps were observed at four nucleotide positions (FIG. 1), with greater than 98.0% sequence identity among the isolates. No variation was observed between the two *P. meibomiae* isolates. A comparison between the *P. pachyrhizi* and *P. meibomiae* ITS1 regions revealed 49 nucleotide differences or gaps (FIG. 1), representing 77.5% sequence identity between these two *Phakopsora* species. The ITS2 region ranged in size from 199–206 nucleotides for the *P. pachyrhizi* isolates, whereas it was found to be 203 and 205 nucleotides for the two *P. meibomiae* isolates, BZ82-1 and PR, respectively. Ten nucleotide differences or gaps were found between the *P. pachyrhizi* isolates (greater than 95.0% identity), while two additional nucleotides were found in the *P. meibomiae* PR isolate relative to the BZ82-1 isolate (greater than 99.0% identity). A comparison of the *P. pachyrhizi* and *P. meibomiae* ITS2 regions revealed 64 nucleotide differences or gaps (FIG. 2) or approximately 68.5% sequence identity between the species.

An alignment of the ITS1 and ITS2 nucleotide sequences of the rust isolates from Hawaii (HW95 and HW98) and Zimbabwe (MUT and TM) with *P. pachyrhizi* and *P. meibomiae* reveals that these isolates are *P. pachyrhizi.*

Example 4

Selection of Species-Specific Primers and the Development of PCR Assays

Since the nucleotide sequence comparisons of the ITS1 and ITS2 regions revealed significant divergence between the *P. pachyrhizi* and *P. meibomiae* isolates, sequence sites were selected for PCR primer design that utilize these differences. Primers of eighteen to twenty-four nucleotides were designed to encompass the nucleotide differences between *P. pachyrhizi* and *P. meibomiae* identified in the ITS1 and ITS2 regions. PCR primers Ppa1, Ppa2, Ppa3, and Ppa4 (for *P. pachyrhizi*) are designed to specifically hybridize to *P. pachyrhizi* sequences, while the primers Pme1 and Pme2 (for *P. meibomiae*) are directed at *P. meibomiae* sequences (FIG. 3, Table 2). The primers Ppm1 and Ppm2 (for *P. pachyrhizi* and *meibomiae*) are aimed at the 5.8S rDNA region that is conserved between *P. pachyrhizi* and *P. meibomiae* (FIG. 3, Table 2). SEQ ID NOs: 3, 5, 7, 9, 11, and 12, representing Ppa1, Ppa3, Pme1, Ppm1, FAM-probe, and VIC®-probe, respectively, appear in FIG. 3 as they are disclosed in the Sequence Listing. Sequences that are disclosed in the Sequence Listing as having SEQ ID NOs: 4, 6, 8, and 10 are complementary to the reverse orientation of the sequences which are identified as Ppa2, Ppa4, Pme2, and Ppm2, respectively, in FIG. 3.

TABLE 2

PCR Primer and Fluorescent Probe Sequences

| | Sequence | SEQ ID NO: | Length | TM* | % GC |
|---|---|---|---|---|---|
| Primer | | | | | |
| Ppa1 | 5'-TAAGATCTTTGGGCAATGGT-3' | 3 | 20 | 53.5 | 40.0 |
| Ppa2 | 5'-GCAACACTCAAAATCCAACAAT-3' | 4 | 22 | 55.4 | 36.4 |
| Ppa3 | 5'-CCCATTTAATTGGCTCATTG-3' | 5 | 20 | 54.4 | 40.0 |
| Ppa4 | 5'-TCAAAATCCAACAATTTCCC-3' | 6 | 20 | 53.7 | 35.0 |
| Pme1 | 5'-GAAGTTTTTGGGCAAATCAC-3' | 7 | 20 | 53.5 | 40.0 |
| Pme2 | 5'-GCACTCAAAATCCAACATGC-3' | 8 | 20 | 55.3 | 45.0 |
| Ppm1 | 5'-GCAGAATTCAGTGAATCATCAAG-3' | 9 | 23 | 55.3 | 39.1 |
| Ppm2 | 5'-CTCAAACAGGTGTACCTTTTGG-3' | 10 | 22 | 55.2 | 45.5 |
| Probe | | | | | |
| FAM- | 5'-FAM-CCAAAAGGTACACCTGTTTGA GTGTCA-TAMRA-3' | 11 | 27 | 63.2 | 44.4 |
| VIC ®- | 5'-VIC ®-TGAACGCACCTTGCACCTTT TGGT-TAMRA-3' | 12 | 24 | 67.3 | 50.0 |

*TM (° C.) was calculated at [50 nM] primer and [50 nM] salt using the program Primer Express Four pairs of PCR primers were selected for specificity to *P. pachyrhizi.* The primer sets, Ppa1/Ppa2, Ppa3/Ppa4, Ppm1/Ppa2, and Ppm1/Ppa4 amplified PCR products of 332, 347, 141, and 136 bp, respectively, from *P. pachyrhizi* isolate TW72-1 but yielded no product from *P. meibomiae* isolate PR (FIGS. 4A, 4B, 4D, and 4E). Two sets of PCR primers were designed specifically for *P. meibomiae*, Pme1/Pme2 and Ppm1/Pme2, that amplified PCR products of 338 and 139 bp, respectively, from *P. meibomiae* isolate PR but not from *P. pachyrhizi* isolate TW72-1 (FIGS. 4C and 4F). The primer set Ppm1/Ppm2 amplified a 79 bp PCR product from both *P. pachyrhizi* isolate TW72-1 and *P. meibomiae* isolate PR (FIG. 4G).

Figure 5:
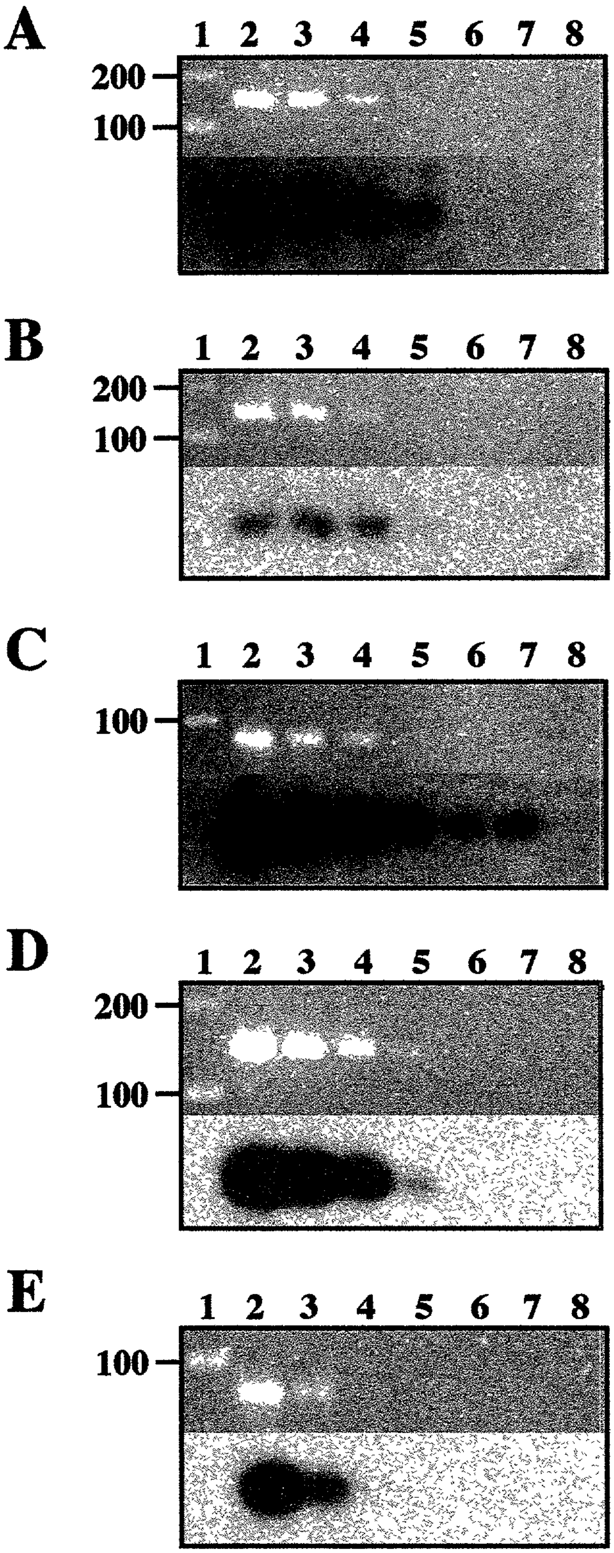
FIG. 5 illustrates the sensitivity of classical PCR assays as detected by agarose gels (top) and Southern blots (bottom): the *P. pachyrhizi*-specific assays include the primer sets: Ppm1/Ppa2 (A) and Ppm1/Ppa4 (B); the *P. meibomiae*-specific assay is shown with the primer set Ppm1/Pme2 (D). The primer combination Ppm1/Ppm2 amplifies a PCR product from both *P. pachyrhizi* and *P. meibomiae* (C and E). DNA dilutions of *P. pachyrhizi* isolate TW72-1 (A, B, and C) and *P. meibomiae* isolate PR (D and E) were used at the following concentrations: 10 ng (2), 1 ng (3), 0.1 ng (4), 10 pg (5), 1 pg (6), and 0.1 pg (7). 1=molecular weight markers (100 bp ladder) and 8=no DNA template control. Hybridization probes used were the ITS regions from TW72-1 (A, B, and C) and BZ82-1 (D and E).

To determine the sensitivity limits of the *P. pachyrhizi*- and *P. meibomiae*-specific assays, dilutions of purified total DNA from *P. pachyrhizi* isolate TW72-1 and *P. meibomiae* isolate PR were tested with the PCR primer sets Ppm1/Ppa2, Ppm1/Ppa4, Ppm1/Pme2, and Ppm1/Ppm2 (FIG. 5). In the

*P. pachyrhizi*-specific assays employing either the primer sets Ppm1/Ppa2 or Ppm1/Ppa4, a PCR product was detected on agarose gels and by Southern blots using as little as 0.1 ng and 10 pg of TW72-1 template DNA, respectively (FIGS. 5A and 5B). The limit of detection was 10 ng of PR template DNA by agarose gel and by Southern blot for the *P. meibomiae*-specific assay with the PCR primer set Ppm1/Pme2 (FIG. 5D). The PCR primer combination Ppm1/Ppm2, which amplifies a DNA product from both *P. pachyrhizi* and *P. meibomiae*, yielded a PCR product on an agarose gel and by a Southern blot using 0.1 ng and 0.1 pg of TW72-1 DNA, respectively (FIG. 5C). However, with this primer pair combination, the sensitivity of detection of a PCR product on both an agarose gel and a Southern blot was reduced to 1 ng of template DNA from *P. meibomiae* isolate PR (FIG. 5E).

Figure 6:
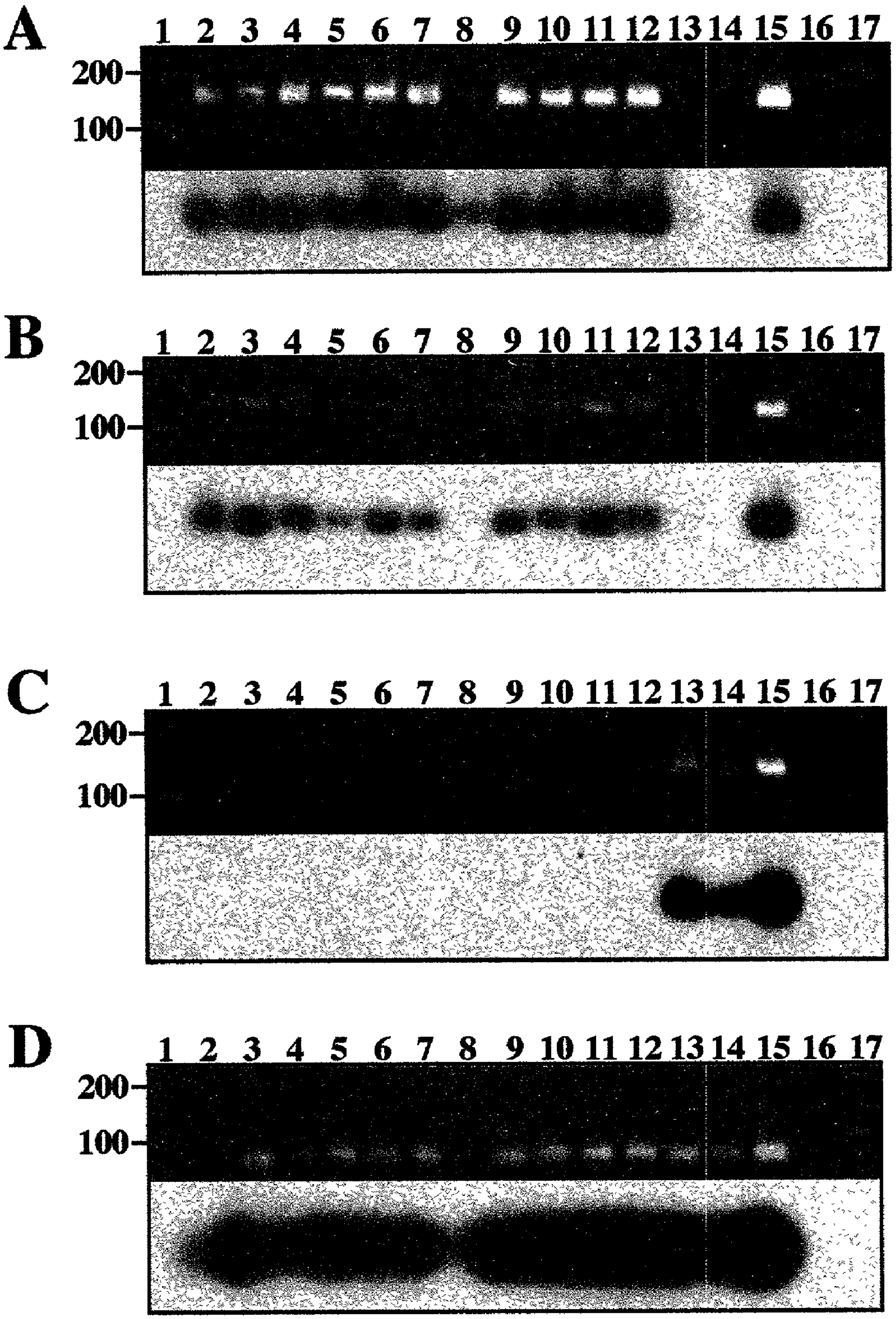
FIG. 6 illustrates classical PCR assays of *P. pachyrhizi* and *P. meibomiae* isolates. Agarose gels (top) and Southern blots (bottom) of *P. pachyrhizi*-specific assays with the primer sets Ppm1/Ppa2 (A) and Ppm1/Ppa4 (B), and of the *P. meibomiae*-specific assay with the primer set Ppm1/Pme2 (C) are shown. The primer combination Ppm1/Ppm2 amplifies a PCR product from both *P. pachyrhizi* and *P. meibomiae* (D). Lanes 1 and 17=molecular weight markers (100 bp ladder), 2=AU72-1, 3=AU79-1, 4=IN73-1, 5=ID72-1, 6=PH77-1, 7=TW72-1, 8=TW80-1, 9=TW80-2, 10=TH, 11=HW95, 12=HW 98, 13=BZ82-1, 14=PR, 15=control plasmid DNA containing the ITS1/2 region from either AU72-1 (A, B, and D) or BZ 82-1 (C), and 16=no DNA template control. Hybridization probes used were the ITS regions from TW72-1 (A, B, and D) and BZ82-1 (C).

To determine the specificity of the *P. pachyrhizi* and *P. meibomiae* PCR primers, crude total DNA extracts from germinating urediniospores of *P. pachyrhizi* and *P. meibomiae* isolates from different geographic regions (Table 1) were tested with the PCR primers. The PCR primers Ppm1/Ppa2 and Ppm1/Ppa4 amplified a PCR product using DNA extracted from all 11 *P. pachyrhizi* isolates, but no PCR product was detected from either of the *P. meibomiae* isolates (FIGS. 6A and 6B). The Ppm1/Pme2 primer set amplified a single PCR product only from DNA extracted from the two *P. meibomiae* isolates, and no PCR product was detected from the *P. pachyrhizi* isolates (FIG. 6C). The primer set Ppm1/Ppm2 amplified a PCR product of 79 bp from each of the *P. pachyrhizi* and *P. meibomiae* isolates tested (FIG. 6D). Southern blots confirmed the identity of the PCR products for each of the PCR assays by hybridization.

Example 5

PCR Assay and Southern Blot Analysis

Oligonucleotide primers specific to *P. pachyrhizi* and *P. meibomiae*, or to both species (Table 2) were synthesized (Life Technologies/GIBCO BRL, Gaithersburg, Md.) to unique sequences within the ITS regions (FIG. 3). Classical PCR reactions were conducted in a Gene AMP PCR System 9700 thermocycler (Applied Biosystems, Inc.) Using 5–25 ng of genomic DNA. PCR assays were performed in a total volume of 25 µl containing: 10 mM Tris-HCl; 50 mM KCl (pH 8.3); 1.5 mM $MgCl_2$0.001% (wt/vol) gelatin; dATP, dGTP, dCTP, and dTTP, each at a concentration of 100 µM; each primer at a concentration of 1.0 µM; and 0.5 U of AmpliTaq DNA polymerase (Applied Biosystems, Inc.). The PCR assays were performed with the following cycling conditions: 94° C. denaturation for 1 min, 25 cycles of 94° C. for 15 s, 65° C. for 15 s, and 72° C. for 15 s, followed by an extension of 72° C. for 6 min.

Negative controls were tested using the same reaction mixture and amplification conditions described above without template DNA. PCR products were analyzed by electrophoresis on 4.0% agarose (3:1 High Resolution Blend, Amresco, Solon, Ohio) gels in 0.5× TBE buffer stained with ethidium bromide (*Current Protocols in Molecular Biology,* 1987, supra). Southern blots, labeling of DNA probes, and hybridization and chemiluminescent detection were as described previously (Frederick et al. 2000. *Phytopath.* 90: 951–960). The ITS region from *P. pachyrhizi* TW 72-1 and *P. meibomiae* PR were used as hybridization probes.

Example 6

TaqMan 5' Nuclease PCR Assay

Real-time PCR assays were developed for the TaqMan system using an internal fluorogenic probe with either the *P. pachyrhizi*-specific primer set Ppm1/Ppa2 or the *P. meibomiae*-specific primer set Ppm1/Pme2. Two different probe sequences common to both species were selected, and one was labeled with FAM and the other with VIC®. The amplicons were 136 and 139 bp for the *P. pachyrhizi*- and *P. meibomiae*-specific assays, respectively (FIG. 3). The primer set Ppm1/Ppm2 yields a 79 bp amplicon using template DNA of either *P. pachyrhizi* or *P. meibomiae*. The 5' nuclease assays were performed using an ABI Prism 7700 Sequence Detection System (Applied Biosystems, Inc.) in a total of 25 µl as described (Frederick et al., supra). The cycling conditions were as follows: 50° C. for 2 min, 95° C. for 10 min, and 35 cycles of 95° C. for 15 s and 60° C. for 1 min. The Ppm1/Ppa2 and Ppm1/Pme2 primer combinations were used at a final concentration of 300 nM with both FAM-probe and VIC ©-probes, while the Ppm1/Ppm2 primer set was used at a final concentration of 900 nM with the VIC®-probe. The TaqMan probes, FAM-probe, and VIC®-probe (Table 2), were labeled at the 5' end with the fluorescent reporter dyes 6-carboxy-fluorescin (FAM) and VIC®, respectively, and both were labeled at the 3' end with the quencher dye, 6-carboxy-tetramethyl-rhodamine (TAMRA) (Applied Biosystems Inc.). The probes were used at 400 nM in both the *P. pachyrhizi*- and *P. meibomiae*-specific assays. The dilution series of genomic DNA from *P. pachyrhizi* isolate TW 72-1 and *P. meibomiae* isolate PR were made in sterile distilled $H_2O$. Two independent replications were analyzed using duplicate DNA samples for each isolate per assay.

Data acquisition and analysis were done using the TaqMan data worksheet and software according to the manufacturer's instructions (Applied Biosystems). The ΔRQ is defined as an increase in the emission intensity ratio of the reporter dye after release from the quencher dye on the fluorescent probe ($RQ^+$) minus the baseline emission intensity of the quenched reporter dye on the intact fluorescent probe ($RQ^-$), or $\Delta RQ=(RQ^+)-(RQ^-)$. The Ct (cycle threshold) values for each reaction were calculated automatically by the ABI Prism sequence detection software by determining the point in time (PCR cycle number) at which the reporter fluorescence exceeds background.

Figure 7:
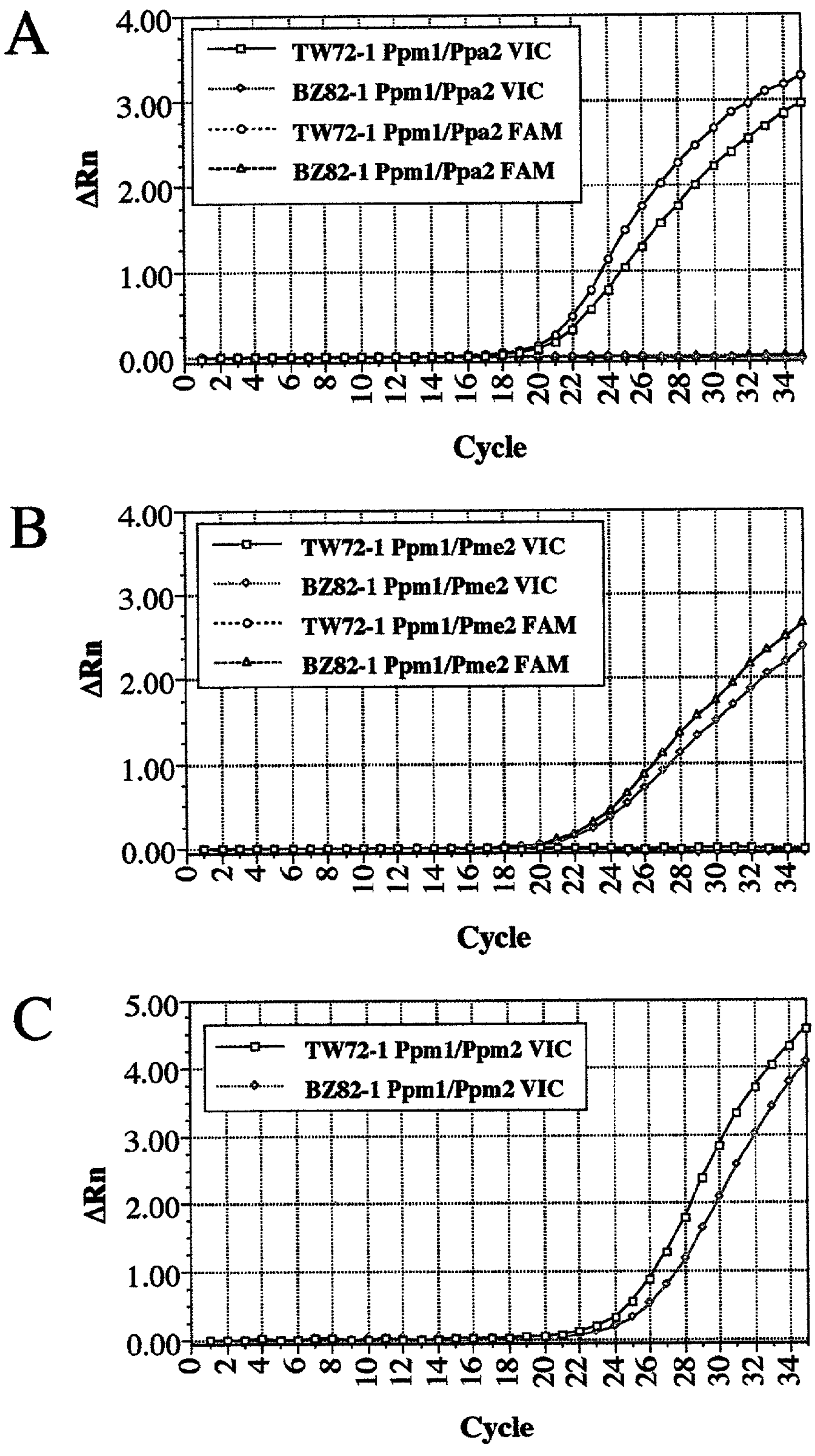
FIG. 7 shows the real-time PCR amplification of DNA from *P. pachyrhizi* isolate TW72-1 and *P. meibomiae* isolate BZ82-1 by TaqMan PCR using an ABI Prism 7700 Sequence Detection System. *P. pachyrhizi*-specific flanking primers Ppm1/Ppa2 (A), *P. meibomiae*-specific flanking primers Ppm1/Pme2 (B) or the primers Ppm1/Ppm2 which amplify a PCR product from both *P. pachyrhizi* and *P. meibomiae* (C) were used with either a 5'-FAM- or 5'-VIC-labeled internal probe sequence. The left axis (ΔRQ) is the change in fluorescence that is a measure of probe cleavage efficiency, and the bottom axis is the PCR cycling stage. Two independent assays were analyzed using duplicate DNA samples for each isolate.

The ΔRQ values were measured following each amplification cycle, and amplification plots of *P. pachyrhizi* isolate TW 72-1 and *P. meibomiae* isolate BZ82-1 are shown for each assay (FIG. 7). In the *P. pachyrhizi*-specific TaqMan assay, the results were similar regardless of the probe used (FIG. 7A). The TW72-1 sample had Ct values of 18.51 (FAM-probe) and 19.36 (VIC®-probe), whereas the BZ82-1 sample had Ct values of greater than 35. The ΔRQ value of the TW72-1 sample assayed with the FAM-probe was slightly higher than with the VIC®-probe (FIG. 7A). In the *P. meibomiae*-specific TaqMan assay (FIG. 7B), the BZ82-1 sample had Ct values of 20.36 (FAM-probe) and 20.60 (VIC®-probe), while the TW72-1 sample had Ct values of greater than 35. Once again, the use of the FAM- or VIC®-probes did not affect Ct values, but the ΔRQ values were slightly higher with the FAM probe (FIG. 7B). Finally, in the TaqMan assay with the Ppm1/Ppm2 primer set and the VIC®-probe, the TW72-1 and BZ82-1 samples had Ct values of 20.32 and 21.69, respectively, and the ΔRQ values of the TW72-1 sample was slightly higher than the BZ82-1 sample (FIG. 7C).

Figure 8:
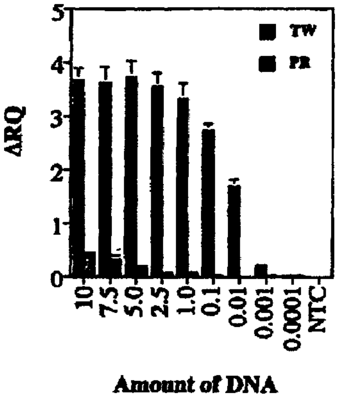
FIG. 8 illustrates the sensitivity of the *P. pachyrhizi*- and *P. meibomiae*-specific real-time PCR assays and the specific amplification of DNA dilutions from *P. pachyrhizi* isolate TW72-1 and *P. meibomiae* isolate PR after 35 cycles of amplification using TaqMan ABI Prism 7700 Sequence Detection System. *P. pachyrhizi*-specific flanking primers Ppm1/Ppa2 were used with a 5'-FAM-labeled internal probe sequence (A), *P. meibomiae*-specific flanking primers Ppm1/Pme2, with a 5'-FAM-labeled internal probe sequence (B), *P. pachyrhizi*-specific flanking primers Ppm1/Ppa2, with a 5'-VIC-labeled internal probe sequence (C), *P. meibomiae*-specific flanking primers Ppm1/Pme2, with a 5'-VIC-labeled internal probe sequence (D), and the primers Ppm1/Ppm2 which amplify a PCR product from both *P. pachyrhizi* and *P. meibomiae*, with a 5'-VIC-labeled internal probe sequence (E). The left axis (ΔRQ) is the change in fluorescence that is a measure of probe cleavage efficiency, and the bottom axis is the PCR cycling stage. The ΔRQ values are the means of two independent assays with duplicate DNA samples for each isolate. Error bars represent standard errors of the means.
Figure 8:
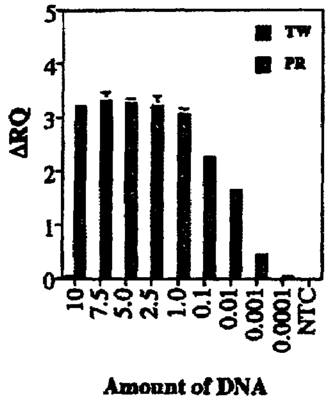
Figure 8:
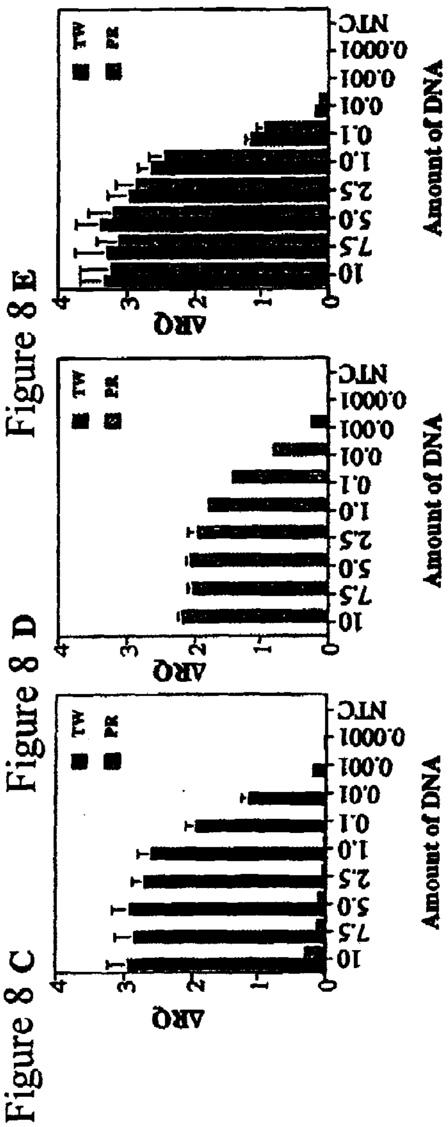

To determine the sensitivity limits of the real-time PCR assays, serial dilutions of purified total DNA of *P. pachyrhizi* isolate TW72-1 and *P. meibomiae* isolate PR were tested as DNA templates in each of the assays (FIG. 8). In the *P. pachyrhizi*-specific assay, 1 pg of total template DNA from TW72-1 produced detectable levels of fluorescence with either the FAM- or VIC®-probes (FIGS. 8A and 8C). Likewise, fluorescence was detected at 1 pg of total DNA from PR in the *P. meibomiae* assay with either probe (FIGS. 8B and 8D). The sensitivity limits were reduced 10-fold (10 pg) for detection of TW72-1 and PR in the TaqMan assay with the primer set Ppm1/Ppm2 and the VIC®-probe (FIG. 8E).

TABLE 3

ΔRQ Values From Real-Time PCR Assays of *P. pachyrhizi* and *P. meibomiae*

| | Ppm1/Ppa2 | | Ppm1/Pme2 | | Ppm1/Ppm2 |
|---|---|---|---|---|---|
| Isolate | FAM-Probe | VIC ®-probe | FAM-probe | VIC ®-probe | VIC ®-probe |
| AU72-1 | 3.555 ± 0.005 | 3.200 ± 0.050 | 0.000 ± 0.000 | 0.000 ± 0.000 | 5.140 ± 00.290 |
| AU79-1 | 3.535 ± 0.025 | 3.365 ± 0.115 | 0.120 ± 0.050 | 0.000 ± 0.000 | 5.110 ± 00.270 |
| IN73-1 | 3.595 ± 0.045 | 3.090 ± 0.090 | 0.000 ± 0.000 | 0.000 ± 0.000 | 5.040 ± 00.340 |
| ID72-1 | 3.480 ± 0.030 | 3.215 ± 0.055 | 0.000 ± 0.000 | 0.000 ± 0.000 | 5.160 ± 00.220 |
| P.H77-1 | 3.490 ± 0.010 | 3.170 ± 0.060 | 0.000 ± 0.000 | 0.000 ± 0.000 | 5.070 ± 00.170 |
| TW72-1 | 3.520 ± 0.000 | 3.345 ± 0.095 | 0.065 ± 0.065 | 0.000 ± 0.000 | 5.100 ± 00.290 |
| TW80-1 | 2.895 ± 0.055 | 2.320 ± 0.020 | 0.390 ± 0.140 | 0.035 ± 0.065 | 2.010 ± 00.360 |
| TW80-2 | 3.605 ± 0.065 | 3.260 ± 0.030 | 0.050 ± 0.055 | 0.020 ± 0.020 | 5.085 ± 00.185 |
| TH | 3.450 ± 0.010 | 3.305 ± 0.105 | 0.000 ± 0.000 | 0.000 ± 0.000 | 5.165 ± 00.195 |
| HW95 | 3.430 ± 0.000 | 3.385 ± 0.085 | 0.055 ± 0.055 | 0.000 ± 0.000 | 5.140 ± 00.270 |
| HW98 | 3.530 ± 0.010 | 3.130 ± 0.100 | 0.810 ± 0.260 | 0.550 ± 0.405 | 5.195 ± 00.225 |
| BZ82-1 | 0.500 ± 0.260 | 0.100 ± 0.030 | 3.310 ± 0.570 | 2.945 ± 0.045 | 5.005 ± 00.185 |
| PR | 0.535 ± 0.465 | 0.735 ± 0.135 | 3.300 ± 0.340 | 2.455 ± 0.015 | 4.355 ± 00.165 |
| NTC* | 0.220 ± 0.220 | 0.360 ± 0.010 | 0.000 ± 0.000 | 0.000 ± 0.000 | 0.400 ± 00.390 |

*NTC = No DNA Template Control

In order to assess the accuracy of the real-time PCR assays, crude DNA extractions from 11 *P. pachyrhizi* and two *P. meibomiae* isolates were tested as templates in the assays. For the *P. pachyrhizi* assay, all 11 *P. pachyrhizi* isolates had ΔRQ values of greater than 2.320, whereas ΔRQ values of the *P. meibomiae* isolates did not exceed 0.735 using either the FAM- or VIC®-probe (Table 3). In addition, all 11 *P. pachyrhizi* isolates had Ct values less than 29.35, while Ct values of the *P. meibomiae* isolates exceeded 35 (Table 4).

TABLE 4

Ct Values From Real-Time PCR Assays of *P. pachyrhizi* and *P. meibomiae*

| | Ppm1/Ppa2 | | Ppm1/Pme2 | | Ppm1/Ppm2 |
|---|---|---|---|---|---|
| Isolate | FAM-probe | VIC ®-probe | FAM-probe | VIC ®-probe | VIC ®-probe |
| AU72-1 | 20.17 ± 0.26 | 21.14 ± 0.08 | >35.00 | >35.00 | 23.29 ± 0.02 |
| AU79-1 | 18.42 ± 0.14 | 19.17 ± 0.10 | >35.00 | >35.00 | 21.35 ± 0.19 |
| IN73-1 | 19.99 ± 0.28 | 20.92 ± 0.47 | >35.00 | >35.00 | 23.77 ± 0.64 |
| ID72-1 | 20.09 ± 0.53 | 21.22 ± 0.17 | >35.00 | >35.00 | 22.24 ± 0.23 |
| P.H77-1 | 20.08 ± 0.06 | 20.83 ± 0.43 | >35.00 | >35.00 | 22.84 ± 0.55 |
| TW72-1 | 18.51 ± 0.18 | 19.37 ± 0.18 | >35.00 | >35.00 | 20.32 ± 0.14 |
| TW80-1 | 27.71 ± 0.38 | 29.35 ± 0.25 | >35.00 | >35.00 | 33.10 ± 0.12 |
| TW80-2 | 20.46 ± 0.68 | 21.72 ± 0.54 | >35.00 | >35.00 | 23.92 ± 0.72 |
| TH | 19.11 ± 0.51 | 20.62 ± 0.07 | >35.00 | >35.00 | 21.86 ± 0.26 |
| HW95 | 19.44 ± 0.21 | 20.03 ± 0.09 | >35.00 | >35.00 | 22.10 ± 0.21 |
| HW98 | 19.68 ± 0.20 | 20.36 ± 0.34 | >35.00 | >35.00 | 21.81 ± 0.12 |
| BZ82-1 | >35.00 | >35.00 | 20.37 ± 0.70 | 20.61 ± 0.29 | 21.69 ± 0.14 |
| PR | >35.00 | >35.00 | 22.53 ± 0.05 | 22.61 ± 0.34 | 26.20 ± 0.11 |
| NTC* | >35.00 | >35.00 | >35.00 | >35.00 | >35.00 |

*NTC = No DNA Template Control

Conversely, in the *P. meibomiae* assay, the *P. meibomiae* isolates had ΔRQ values greater than 2.455, while the ΔRQ values of the *P. pachyrhizi* isolates did not exceed 0.810 (Table 3). Furthermore, the *P. meibomiae* isolates had Ct values of less than 22.61, whereas the Ct values of the *P. pachyrhizi* isolates were greater than 35 (Table 4). Finally, in the TaqMan assay with the Ppm1/Ppm2 primers, the ΔRQ values exceeded 2.010 for all of the *P. pachyrhizi* and *P. meibomiae* isolates, compared to 0.400 for the no template control (Table 3).

Example 7

Detection of *Phakopsora* spp. from Infected Plant

Figure 9:
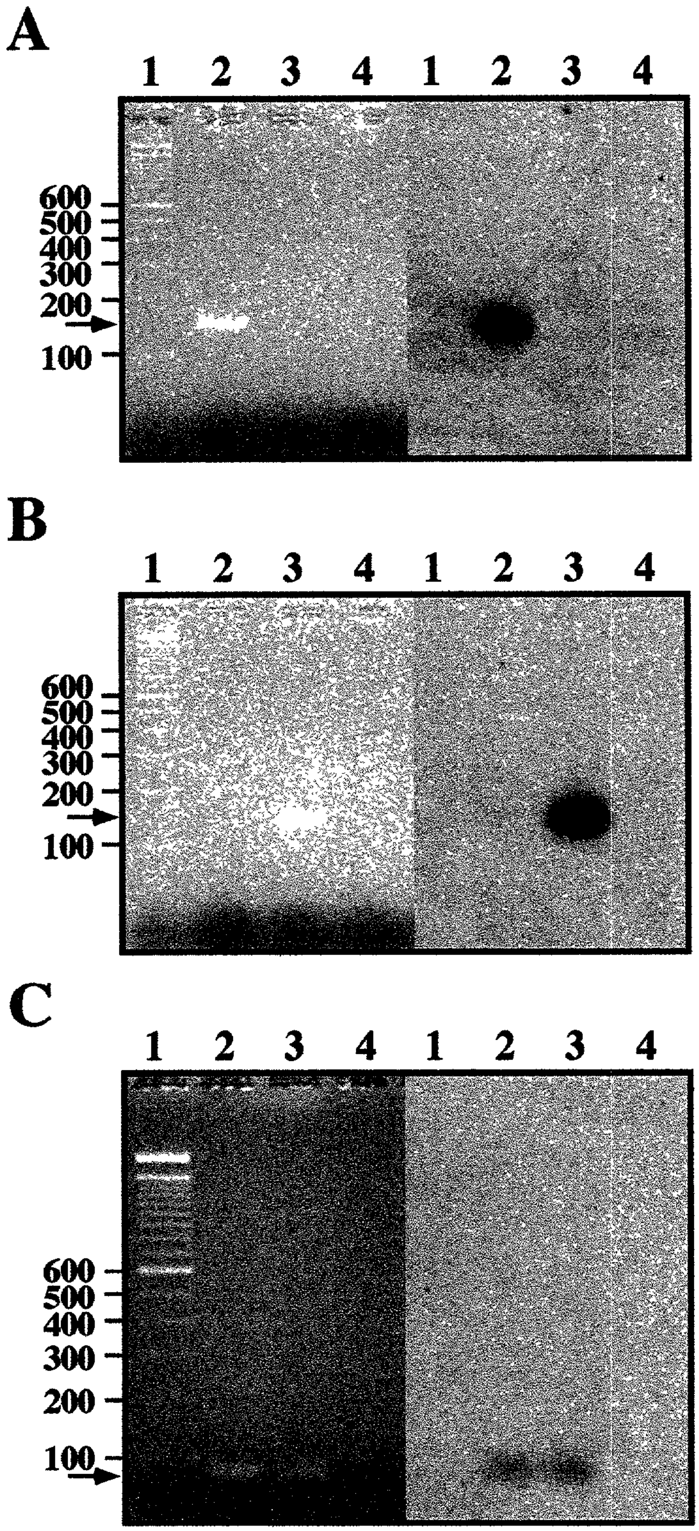
FIG. 9 shows the detection of *P. pachyrhizi* and *P. meibomiae* from infected leaves using classical PCR. Agarose gels (left) and Southern blots (right) of the *P. pachyrhizi*-specific assay using primer set Ppm1/Ppa2 (A), the *P. meibomiae*-specific assay with the primer set Ppm1/Pme2 (B), and the non-specific primers Ppm1/Ppm2 (C) are shown. Lane 1=molecular weight markers (100 bp), 2=soybean infected with *P. pachyrhizi* isolate TW72-1, 3=soybean infected with *P. meibomiae* isolate BZ82-1, and 4=healthy soybean. PCR products are indicated by arrows.

The classical and real-time PCR assays were evaluated using infected soybean leaf tissue. In the *P. pachyrhizi*-specific classical PCR assay, soybean plants infected with *P. pachyrhizi* isolate TW72-1 produced a visible PCR product on an agarose gel and Southern blot, whereas the plants infected with *P. meibomiae* isolate BZ82-1 did not (FIG. 9A). Conversely, soybean plants infected with *P. meibomiae* isolate BZ82-1 yielded a DNA band on an agarose gel and Southern blot using the *P. meibomiae*-specific PCR assay, but no band was detected from the plants infected with *P. pachyrhizi* isolate TW72-1 (FIG. 9B). The PCR assay with the primer set Ppm1/Ppm2 revealed a PCR product from soybean plants infected with either *P. pachyrhizi* isolate TW72-1 or *P. meibomiae* isolate BZ82-1 (FIG. 9C).

Figure 10:
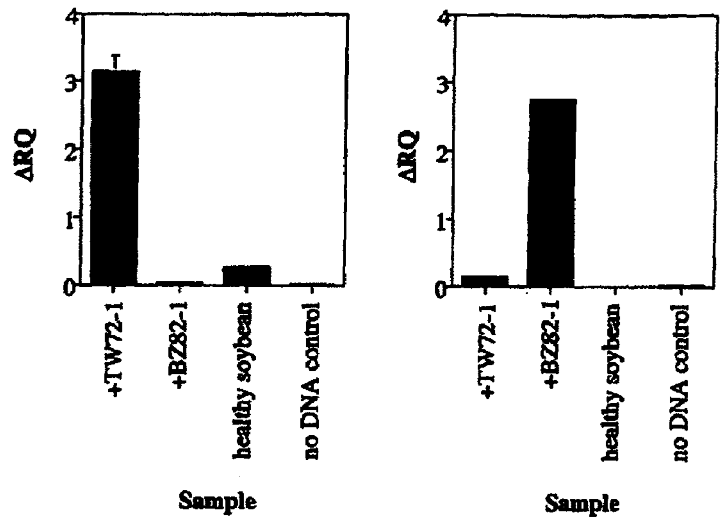
FIG. 10 illustrates the detection of *P. pachyrhizi* and *P. meibomiae* from infected leaves using real-time PCR. PCR assays were conducted for 35 cycles using a TaqMan ABI Prism 7700 Sequence Detection System with *P. pachyrhizi*-specific flanking primers Ppm1/Ppa2 with a 5'-FAM-labeled internal probe sequence (A), *P. meibomiae*-specific flanking primers Ppm1/Pme2 with a 5'-FAM-labeled internal probe sequence (B), *P. pachyrhizi*-specific flanking primers Ppm1/Ppa2 with a 5'-VIC-labeled internal probe sequence (C), *P. meibomiae*-specific flanking primers Ppm1/Pme2 with a 5'-VIC-labeled internal probe sequence (D), or the primers Ppm1/Ppm2 which amplify a PCR product from both *P. pachyrhizi* and *P. meibomiae* with a 5'-VIC-labeled internal probe sequence (E). The left axis (ΔRQ) is the change in fluorescence that is a measure of probe cleavage efficiency, and the bottom axis is the PCR cycling stage. The ΔRQ values are the means of two independent assays with duplicate DNA samples for each isolate. Error bars represent standard errors of the means. +TW72-1=soybean infected with *P. pachyrhizi* isolate TW72-1, +BZ82-1=soybean infected with *P. meibomiae* isolate BZ82-1, healthy soybean=non-inoculated soybean, and NTC=no DNA template control.
Figure 10:
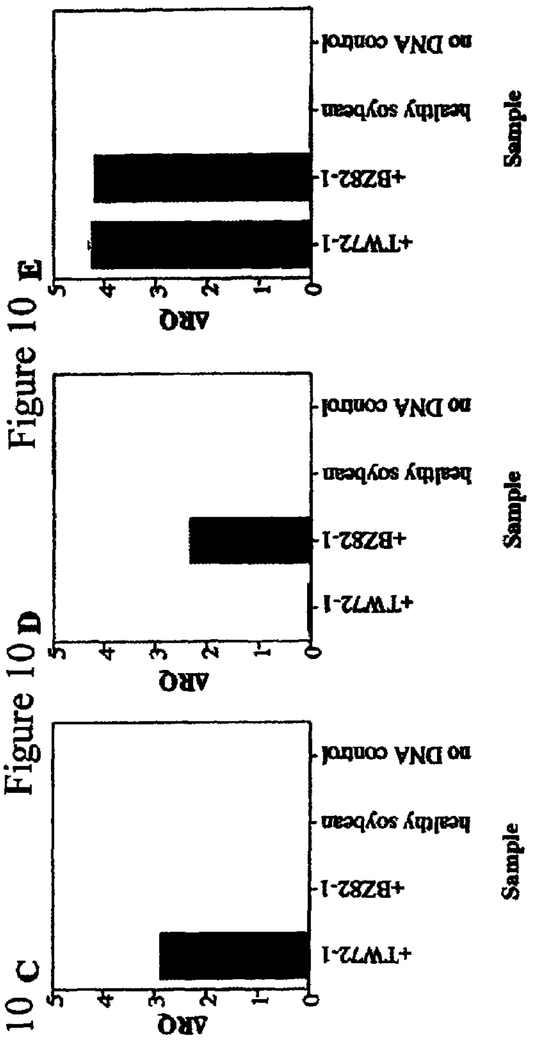

In the *P. pachyrhizi* real-time PCR assay, the DNA sample extracted from soybean infected with *P. pachyrhizi* isolate TW72-1 had ΔRQ values of 3.095 and 2.810 with the FAM- and VIC®-probes, respectively (FIGS. 10A and 10C). The DNA sample from soybean infected with *P. meibomiae* isolate BZ82-1 had ΔRQ values of 0.290 with the FAM-probe and 0.050 with the VIC®-probe (FIGS. 10A and 10C). The Ct values of the plants infected with TW72-1 were 18.57±0.14 (FAM-probe) and 20.73±0.21 (VIC®-probe), while the Ct values of the plants infected with BZ82-1 and the non-inoculated control plants were greater than 35 for both the FAM- and VIC®-probes. On the other hand, the DNA sample extracted from soybean infected with *P. meibomiae* isolate BZ82-1 had ΔRQ values of 2.970 with the FAM-probe and 3.085 with the VIC®-probe using the *P. meibomiae* real-time PCR assay (FIGS. 10B and 10D). The DNA sample from soybean infected with *P. pachyrhizi* isolate TW72-1 had ΔRQ values of 0.320 and 0.245 with the FAM- and VIC®-probes, respectively (FIGS. 10B and 10D). The Ct values of the plants infected with BZ82-1 were 19.05±0.04 (FAM-probe) and 20.89±0.10 (VIC®-probe), while the Ct values of the plants infected with TW72-1 and the non-inoculated control plants were greater than 35 for both the FAM- and VIC®-probes. In the real-time PCR assays with the primer set Ppm1/Ppm2, the DNA samples extracted from soybean infected with either *P. pachyrhizi* isolate TW72-1 or *P. meibomiae* isolate BZ82-1 had ΔRQ values of 4.450 and 4.225 with the VIC®-probe, respectively (FIG. 10E). The Ct values of the plants infected with TW72-1 and BZ82-1 were 22.07±0.18 and 22.14±0.28, respectively, while the Ct value of non-inoculated control plants was greater than 35.

NUCLEOTIDE SEQUENCE ACCESSION NUMBERS

The nucleotide sequence of the ITS1-5.8S-ITS-2 regions from the *P. pachyrhizi* and *P. meibomiae* isolates from this study have been deposited at GenBank and have been assigned the accession numbers AF333488-AF333502.

All publications and patents mentioned in this specification are herein incorporated by reference to the same extent as if each individual publication or patent was specifically and individually indicated to be incorporated by reference.

The foregoing description and certain representative embodiments and details of the invention have been presented for purposes of illustration and description of the invention. It is not intended to be exhaustive or to limit the invention to the precise forms disclosed. It will be apparent to practitioners skilled in this art that modifications and variations may be made therein without departing from the scope of the invention.

I claim:

1. A primer set comprising oligonucleotide primers consisting of an eighteen to twenty-four nucleotide contiguous portion of SEQ ID NO:2 or of its complement, wherein said primer set comprises the contiguous sequence 5'-TAAGATCTTTGGGCAATGGT-3' (SEQ ID NO:3) and the sequence 5'-GCAACACTCAAAATCCAACAAT-3' (SEQ ID NO:4) or at least an eighteen nucleotide contiguous portion of SEQ ID NO: 3 and SEQ ID NO:4, and wherein said primer set encompasses at least a single nucleotide difference between *P. pachyrhizi* and *P. meibomiae* at the 3' terminus of the primer when the ITS1 or ITS2 regions are aligned and when a comparison as depicted in FIG. 3 is made between said ITS1 or ITS2 regions, and wherein said primer set specifically hybridizes to a region of SEQ ID NO:2 or its complement, and wherein said primer set distinguishes *P. pachyrhizi* from *P. meibomiae.*

2. A primer set comprising oligonucleotide primers consisting of an eighteen to twenty-four nucleotide contiguous portion of SEQ ID NO:2 or of its complement, wherein said primer set comprises the contiguous sequence 5'-GCAGAATTCAGTGAATCATCAAG-3' (SEQ ID NO:9) and the sequence 5'-GCAACACTCAAAATCCAACAAT-3' (SEQ ID NO:4) or at least an eighteen nucleotide contiguous portion of SEQ ID NO: 9 and SEQ ID NO:4, and wherein said primer set encompasses at least a single nucleotide difference between *P. pachyrhizi* and *P. meibomiae* at the 3' terminus of the primer when the ITS1 or ITS2 regions are aligned and when a comparison as depicted in FIG. 3 is made between said ITS1 or ITS2 regions, and wherein said primer set specifically hybridizes to a region of SEQ ID NO:2 or its complement, and wherein said primer set distinguishes *P. pachyrhizi* from *P. meibomiae.*

3. A primer set comprising oligonucleotide primers consisting of an eighteen to twenty-four nucleotide contiguous portion of SEQ ID NO:2 or of its complement, wherein said primer set comprises the contiguous sequence 5'-CCCATTTAATTGGCTCATTG-3' (SEQ ID NO:5) and the sequence 5'-TCAAAATCCAACAATTTCCC-3' (SEQ ID NO:6) or at least an eighteen nucleotide contiguous portion of SEQ ID NO:5 and SEQ ID NO:6, and wherein said primer set encompasses at least a single nucleotide difference between *P. pachyrhizi* and *P. meibomiae* at the 3' terminus of the primer when the ITS1 or ITS2 regions are aligned and when a comparison as depicted in FIG. 3 is made between said ITS1 or ITS2 regions, and wherein said primer set specifically hybridizes to a region of SEQ ID NO:2 or its complement, and wherein said primer set distinguishes *P. pachyrhizi* from *P. meibomiae.*

4. A primer set comprising oligonucleotide primers consisting of an eighteen to twenty-four nucleotide contiguous portion of SEQ ID NO:2 or of its complement, wherein said primer set comprises the contiguous sequence 5'-GCAGAATTCAGTGAATCATCAAG-3' (SEQ ID NO:9) and the sequence 5'-TCAAAATCCAACAATTTCCC-3' (SEQ ID NO:6) or at least an eighteen nucleotide contiguous portion of SEQ ID NO: 9 and SEQ ID NO:6, and wherein said primer set encompasses at least a single nucleotide difference between *P. pachyrhizi* and *P. meibomiae* at the 3' terminus of the primer when the ITS1, or ITS2 regions are aligned and when a comparison as depicted in FIG. 3 is made between said ITS1 or ITS2 regions, and wherein said primer set specifically hybridizes to a region of SEQ ID NO:2 or its complement, and wherein said primer set distinguishes *P. pachyrhizi* from *P. meibomiae.*

5. A primer set comprising oligonucleotide primers consisting of an eighteen to twenty-four nucleotide contiguous portion of SEQ ID NO:2 or of its complement, wherein said primer set comprises the contiguous sequence 5'-GCAGAATTCAGTGAATCATCAAG-3' (SEQ ID NO:9) and the sequence 5'-GCACTCAAAATCCAACATGC-3' (SEQ ID NO:8) or at least an eighteen nucleotide contiguous portion of SEQ ID NO:9 and SEQ ID NO:8, and wherein said primer set encompasses at least a single nucleotide difference between *P. pachyrhizi* and *P. meibomiae* at the 3' terminus of the primer when the ITS1 or ITS2 regions are aligned and when a comparison as depicted in FIG. 3 is made between said ITS1 or ITS2 regions, and wherein said primer set specifically hybridizes to a region of SEQ ID NO:2 or its complement, and wherein said primer set distinguishes *P. pachyrhizi* from *P. meibomiae.*

6. An oligonucleotide primer consisting of an eighteen to twenty-four nucleotide contiguous portion of SEQ ID NO:2 or of its complement, wherein said eighteen to twenty-four nucleotides of said primer comprises the contiguous twenty-three nucleotide sequence 5'-GCAGAATTCAGTGAAT-CATCAAG-3' (SEQ ID NO:9) or an eighteen to twenty-two nucleotide contiguous portion of SEQ ID NO:9, and wherein said primer specifically hybridizes to a region of SEQ ID NO:2 or its complement, and wherein said primer identifies *P. pachyrhizi* and *P. meibomiae.*

7. A primer set comprising oligonucleotide primers consisting of an eighteen to twenty-four nucleotide contiguous portion of SEQ ID NO:2 or of its complement, wherein said primer set comprises the contiguous sequence 5'-GCA-GAATTCAGTGAATCATCAAG-3' (SEQ ID NO:9) and the sequence 5'-CTCAAACAGGTGTACCTTTTGG-3' (SEQ ID NO:10) or at least an eighteen nucleotide contiguous portion of SEQ ID NO:9 and SEQ ID NO:10, and wherein said primer set encompasses at least a single nucleotide difference between *P. pachyrhizi* and *P. meibomiae* at the 3' terminus of the primer when the ITS1 or ITS2 regions are aligned and when a comparison as depicted in FIG. 3 is made between said ITS1 or ITS2 regions, and wherein said primer set specifically hybridizes to a region of SEQ ID NO:2 or its complement, and wherein said primer set distinguishes *P. pachyrhizi* from *P. meibomiae.*

8. A probe comprising a detectable label conjugated to an oligonucleotide consisting of SEQ ID NO:11.

9. A probe comprising a detectable label conjugated to an oligonucleotide consisting of SEQ ID NO:12.

10. A method of detecting the presence of *P. pachyrhizi* by polymerase chain reaction, said method comprising:

a) providing DNA of *P. pachyrhizi* or a test sample suspected of containing DNA of said *P. pachyrhizi;* b) amplifying a target sequence of DNA of said *P. pachyrhizi* using at least one oligonucleotide primer consisting of an eighteen to twenty-four nucleotide contiguous portion of SEQ ID NO:2 or of its complement, wherein said eighteen to twenty-four contiguous nucleotides of said primer is selected from the group consisting of the contiguous twenty nucleotide sequence 5'-TAAGATCTTTGG GCAATGGT-3' (SEQ ID NO:3), the contiguous twenty-two nucleotide sequence 5'-GCAACACTCAAAATCCAACAAT-3' (SEQ ID NO:4), the contiguous twenty nucleotide sequence 5'-CCCATTTAATTGGCTCATTG-3' (SEQ ID NO:5), the contiguous twenty nucleotide sequence 5'-TCAAAATCCAACAATTTCCC-3' (SEQ ID NO:6) and at least an eighteen nucleotide contiguous portion of SEQ ID NO: 3, 4, 5, or 6, and wherein said primer encompasses at least a single nucleotide difference between *P. pachyrhizi* and *P. meibomiae* at the 3' terminus of the primer when the ITS1 or ITS2 regions are aligned and when a comparison as depicted in FIG. 3 is made between said ITS1 or ITS2 regions, and wherein the primer specifically hybridizes to a region of SEQ ID NO:2 or its complement, and wherein the primer distinguishes *P. pachyrhizi* from *P. meibomiae* and c) detecting the presence of amplification products of the target sequence of DNA as an indication of the presence of *P. pachyrhizi.*

11. A method of detecting the presence of *P. pachyrhizi* by polymerase chain reaction, said method comprising:

a) providing DNA of *P. pachyrhizi* or a test sample suspected of containing DNA of said *P. pachyrhizi,* b) amplifying a target sequence of DNA of said *P. pachyrhizi* using a primer set comprising oligonucleotide primers consisting of an eighteen to twenty-four nucleotide contiguous portion of SEQ ID NO:2 or of its complement, wherein said primer set comprises the contiguous sequence 5'-TAA-GATCTTTGGGCAAGGT-3' (SEQ ID NO:3) and the contiguous sequence 5'-GCAACACTCAAAATC CAACAAT-3' (SEQ ID NO:4) or at least an eighteen nucleotide contiguous portion of SEQ ID NO: 3 and SEQ ID NO:4, and wherein said primer set encompasses at least a single nucleotide difference between *P. pachyrhizi* and *P. meibomiae* at the 3' terminus of the primer when the ITS1 or ITS2 regions are aligned and when a comparison as depicted in FIG. 3 is made between said ITS1 or ITS2 regions, and wherein said primer set specifically hybridizes to a region of SEQ ID NO:2 or its complement, and wherein said primer set distinguishes *P. pachyrhizi* from *P. meibomiae*; and c) detecting the presence of amplification products of the target sequence of DNA as an indication of the presence of *P. pachyrhizi.*

12. A method of detecting the presence of *P. pachyrhizi* by polymerase chain reaction, said method comprising:

a) providing DNA of *P. pachyrhizi* or a test sample suspected of containing DNA of said *P. pachyrhizi;* b) amplifying a target sequence of DNA of said *P. pachyrhizi* using a primer set comprising oligonucleotide primers consisting of an eighteen to twenty-four nucleotide contiguous portion of SEQ ID NO:2 or of its complement, wherein said primer set comprises the contiguous sequence 5'-GCAGAATTCAGTGAAT CACAAG-3' (SEQ ID NO:9) and the contiguous sequence 5'-GCAACACTCAAA ATCCAACAAT-3' (SEQ ID NO:4) or at least an eighteen nucleotide contiguous portion of SEQ ID NO: 9 and SEQ ID NO:4, and wherein said primer set encompasses at least a single nucleotide difference between *P. pachyrhizi* and *P. meibomiae* at the 3' terminus of the primer when the ITS1 or ITS2 regions are aligned and when a comparison as depicted in FIG. 3 is made between said ITS1 or ITS2 regions, and wherein said primer set specifically hybridizes to a region of SEQ ID NO:2 or its complement, and wherein said primer set distinguishes *P. pachyrhizi* from *P. meibomiae*; and c) detecting the presence of amplification products of the target sequence of DNA as an indication of the presence of *P. pachyrhizi.*

13. A method of detecting the presence of *P. pachyrhizi* by polymerase chain reaction, said method comprising:

a) providing DNA of *P. pachyrhizi* or a test sample suspected of containing DNA of said *P. pachyrhizi;* b) amplifying a target sequence of DNA of said *P. pachyrhizi* using a primer set comprising oligonucleotide primers consisting of an eighteen to twenty-four nucleotide contiguous portion of SEQ ID NO:2 or of its complement, wherein said primer set comprises the contiguous sequence 5'-CCCATTTAATTGGCTCA TTG-3' (SEQ ID NO:5) and the contiguous sequence 5'-TCAAAATCCAACAATT TCCC-3' (SEQ ID NO:6)

or at least an eighteen nucleotide contiguous portion of SEQ ID NO: 5 and SEQ ID NO:6, and wherein said primer set encompasses at least a single nucleotide difference between *P. pachyrhizi* and *P. meibomiae* at the 3' terminus of the primer when the ITS1 or ITS2 regions are aligned and when a comparison as depicted in FIG. 3 is made between said ITS1 or ITS2 regions, and wherein said primer set specifically hybridizes to a region of SEQ ID NO:2 or its complement, and wherein said primer set distinguishes *P. pachyrhizi* from *P. meibomiae*; and c) detecting the presence of amplification products of the target sequence of DNA as an indication of the presence of *P. pachyrhizi.*

14. A method of detecting the presence of *P. pachyrhizi* by polymerase chain reaction, said method comprising:

a) providing DNA of *P. pachyrhizi* or a test sample suspected of containing DNA of said *P. pachyrhizi;* b) amplifying a target sequence of DNA of said *P. pachyrhizi* using a primer set comprising oligonucleotide primers consisting of an eighteen to twenty-four nucleotide contiguous portion of SEQ ID NO:2 or of its complement, wherein said primer set comprises the contiguous sequence 5'-GCAGAATTCAGTGAAT CATCAAG-3' (SEQ ID NO:9) and the contiguous sequence 5'-TCAAAATCCAA CAATTTCCC-3' (SEQ ID NO:6) or at least an eighteen nucleotide contiguous portion of SEQ ID NO: 9 and SEQ ID NO:6, and wherein said primer set encompasses at least a single nucleotide difference between *P. pachyrhizi* and *P. meibomiae* at the 3' terminus of the primer when the ITS 1 or ITS2 regions are aligned and when a comparison as depicted in FIG. 3 is made between said ITS1 or ITS2 regions, and wherein said primer set specifically hybridizes to a region of SEQ ID NO:2 or its complement, and wherein said primer set distinguishes *P. pachyrhizi* from *P. meibomiae*; and c) detecting the presence of amplification products of the target sequence of DNA as an indication of the presence of *P. pachyrhizi.*

15. The method of any one of claims 12 and 14, wherein amplification takes place under real-time PCR conditions and the amplification products are detected and quantitated by real-time analysis.

16. A method of identifying *P. pachyrhizi* and *P. meibomiae* by polymerase chain reaction, said method comprising:

a) providing DNA of *P. pachyrhizi* and *P. meibomiae* or a test sample suspected of containing DNA of said *P. pachyrhizi* and *P. meibomiae;* b) amplifying a target sequence of DNA of said *P. pachyrhizi* and *P. meibomiae* using a primer set comprising oligonucleotide primers consisting of an eighteen to twenty-four nucleotide contiguous portion of SEQ ID NO:2 or of its complement, wherein said primer set comprises the contiguous sequence 5'-GC AGAATTCAGTGAATCATCAAG-3' (SEQ ID NO:9) and the contiguous sequence 5'-CTCAAACAGGTGTACCTTTTGG-3' (SEQ ID NO: 10) or at least an eighteen nucleotide contiguous portion of SEQ ID NO: 9 and SEQ ID NO:10, and wherein said primer set encompasses at least a single nucleotide difference between *P. pachyrhizi* and *P. meibomiae* at the 3' terminus of the primer when the ITS1 or ITS2 regions are aligned and when a comparison as depicted in FIG. 3 is made between said ITS1 or ITS2 regions, and wherein said primer set specifically hybridizes to a region of SEQ ID NO:2 or its complement, and wherein said primer set identifies *P. pachyrhizi* and *P. meibomiae*; and c) detecting the presence of amplification products of the target sequence of DNA as an indication of the presence of *P. pachyrhizi* and *P. meibomiae.*

17. A kit for detecting the presence of *P. pachyrhizi* comprising at least one oligonucleotide primer consisting of an eighteen to twenty-four nucleotide contiguous portion of SEQ ID NO:2 or of its complement, wherein said eighteen to twenty-four contiguous nucleotides of said primer is selected from the group consisting of the contiguous twenty nucleotide sequence 5'-TAAGATCTTTGGGCAATGGT-3' (SEQ ID NO:3), the contiguous twenty-two nucleotide sequence 5'-GCAACACTCAAAATCCAACAAT-3' (SEQ ID NO:4), an oligonucleotide primer comprising the contiguous twenty nucleotide sequence 5'-CCCATTTAATTGGCTCATTG-3' (SEQ ID NO:5), an oligonucletide primer comprising the contiguous twenty nucleotide sequence 5'-TCAAAATCCAACAATTTCCC-3' (SEQ ID NO:6) and at least an eighteen nucleotide contiguous portion of SEQ ID NO: 3, 4, 5, or 6, and wherein said primer encompasses at least a single nucleotide difference between *P. pachyrhizi* and *P. meibomiae* at the 3' terminus of the primer when the ITS1 or ITS2 regions are aligned and when a comparison as depicted in FIG. 3 is made between said ITS1 or ITS2 regions, and wherein said primer specifically hybridizes to a region of SEQ ID NO:2 or Its complement, and wherein said primer distinguishes *P. pachyrhizi* from *P. meibomiae.*

18. An oligonucleotide primer consisting of an eighteen to twenty-four nucleotide contiguous portion of SEQ ID NO:2 or of its complement, wherein the primer is a contiguous nucleotide sequence of the ITS1 or the ITS2 region of SEQ ID NO:2, said ITS1 region consisting of a nucleotide sequence beginning at nucleotide 55 and ending at nucleotide 253 of SEQ ID NO: 2 as depicted in FIG. 3A and said ITS2 region consisting of a nucleotide sequence beginning at nucleotide 408 and ending at nucleotide 609 of SEQ ID NO: 2 as depicted in FIG. 3B, wherein said contiguous nucleotide sequence of the primer encompasses at least a single nucleotide difference between *P. pachyrhizi* and *P. meibomiae* when said ITS1 or ITS2 regions are aligned and when a comparison as depicted in FIG. 3 is made between said ITS1 or ITS2 regions, and wherein the primer specifically hybridizes to a region of SEQ ID NO:2 or its complement and wherein the primer distinguishes *P. pachyrhizi* from *P. meibomiae.*

19. An oligonucleotide primer consisting of an eighteen to twenty-four nucleotide contiguous portion of SEQ ID NO:2 or of its complement, wherein said eighteen to twenty-four nucleotides of said primer comprises the contiguous twenty nucleotide sequence 5'-TAAGATCTTTGGGCAATGGT-3' (SEQ ID NO:3) or at least an eighteen nucleotide contiguous portion of SEQ ID NO: 3, and wherein said primer encompasses at least a single nucleotide difference between *P. pachyrhizi* and *P. meibomiae* at the 3' terminus of the primer when the ITS1 or ITS2 regions are aligned and when a comparison as depicted in FIG. 3 is made between said ITS1 or ITS2 regions, and wherein said primer specifically hybridizes to a region of SEQ ID NO:2 or its complement, and wherein said primer distinguishes *P. pachyrhizi* from *P. meibomiae.*

20. An oligonucleotide primer consisting of an eighteen to twenty-four nucleotide contiguous portion of SEQ ID NO:2 or of its complement, wherein said eighteen to twenty-four nucleotides of said primer comprises the contiguous twenty-two nucleotide sequence 5'-GCAACACTCAAAATCCAA- CAAT-3' (SEQ ID NO:4) or at least an eighteen nucleotide contiguous portion of SEQ ID NO: 4, and wherein said primer encompasses at least a single nucleotide difference between *P. pachyrhizi* and *P. meibomiae* at the 3' terminus of the primer when the ITS1 or ITS2 regions are aligned and when a comparison as depicted in FIG. 3 is made between said ITS1 or ITS2 regions, and wherein said primer specifically hybridizes to a region of SEQ ID NO:2 or its complement, and wherein said primer distinguishes *P. pachyrhizi* from *P. meibomiae.*

21. An oligonucleotide primer consisting of an eighteen to twenty-four nucleotide contiguous portion of SEQ ID NO:2 or of its complement, wherein said eighteen to twenty-four nucleotides of said primer comprises the contiguous twenty nucleotide sequence 5'-CCCATTTAATTGGCTCATTG-3' (SEQ ID NO:5) or at least an eighteen nucleotide contiguous portion of SEQ ID NO: 5, and wherein said primer encompasses at least a single nucleotide difference between *P. pachyrhizi* and *P. meibomiae* at the 3' terminus of the primer when the ITS 1 or ITS2 regions are aligned and when a comparison as depicted in FIG. 3 is made between said ITS1 or ITS2 regions, and wherein said primer specifically hybridizes to a region of SEQ ID NO:2 or its complement, and wherein said primer distinguishes *P. pachyrhizi* from *P. meibomiae.*

22. An oligonucleotide primer consisting of an eighteen to twenty-four nucleotide contiguous portion of SEQ ID NO:2 or of its complement, wherein said eighteen to twenty-four nucleotides of said primer comprises the contiguous twenty nucleotide sequence 5'-TCAAAATCCAACAATTTCCC-3' (SEQ ID NO:6) or at least an eighteen nucleotide contiguous portion of SEQ ID NO: 6, and wherein said primer encompasses at least a single nucleotide difference between *P. pachyrhizi* and *P. meibomiae* at the 3' terminus of the primer when the ITS1 or ITS2 regions are aligned and when a comparison as depicted in FIG. 3 is made between said ITS1 or ITS2 regions, and wherein said primer specifically hybridizes to a region of SEQ ID NO:2 or its complement, and wherein said primer distinguishes *P. pachyrhizi* from *P. meibomiae.*

23. An oligonucleotide primer consisting of an eighteen to twenty-four nucleotide contiguous portion of SEQ ID NO:2 or of its complement, wherein said eighteen to twenty-four nucleotides of said primer comprises the contiguous twenty-two nucleotide sequence 5'-CTCAAACAGGTGTAC-CTTTTGG-3' (SEQ ID NO:10) or at least an eighteen nucleotide contiguous portion of SEQ ID NO:10, and wherein said primer specifically hybridizes to a region of SEQ ID NO:2 or its complement, and wherein said primer identifies *P. pachyrhizi* and *P. meibomiae.*

24. An oligonucleotide consisting of SEQ ID NO:2.

25. A probe for the detection of a target sequence of DNA of *P. pachyrhizi* and *P. meibomiae*, wherein said probe consists of about a twenty to thirty nucleotide contiguous portion of the ITS1, the 5.8S rDNA region, or the ITS2 region of SEQ ID NO:2 said ITS1 region consisting of a nucleotide sequence beginning at nucleotide 55 and ending at nucleotide 253 of SEQ ID NO: 2 as depicted in FIG. 3A, said 5.8S rDNA region consisting of a nucleotide sequence beginning at nucleotide 254 and ending at nucleotide 407 of SEQ ID NO:2 as depicted in FIGS. 3A and 3B, and said ITS2 region consisting of a nucleotide sequence beginning at nucleotide 408 and ending at nucleotide 609 of SEQ ID NO: 2 as depicted in FIG. 3B, wherein said contiguous portion is revealed to be identical when a comparison between *P. pachyrhizi* and *P. meibomiae* is made, as depicted in FIG. 3, wherein said twenty to thirty contiguous nucleotides of said probe is conjugated to a detectable label, and wherein said probe specifically hybridizes to said portion of SEQ ID NO:2 or its complement.

26. A kit for detecting the presence of *P. pachyrhizi* and *P. meibomiae* consisting of an oligonucleotide primer consisting of an eighteen to twenty-four nucleotide contiguous portion of SEQ ID NO:2 or of its complement, wherein said eighteen to twenty-four contiguous nucleotides of said primer comprises the contiguous twenty-three nucleotide sequence 5'-GCAGAATTCAGTGAATCATCAAG-3' (SEQ ID NO:9) or at least an eighteen nucleotide contiguous portion of SEQ ID NO:9 for use in real-time PCR and a probe for the detection of a target sequence of DNA of *P. pachyrhizi* and *P. meibomiae*, wherein said probe consists of about a twenty to thirty nucleotide contiguous portion of the ITS1, the 5.85 rDNA region, or the ITS2 region of SEQ ID NO:2, said ITS1 region consisting of a nucleotide sequence beginning at nucleotide 55 and ending at nucleotide 253 of SEQ ID NO: 2 as depicted in FIG. 3A, said 5.85 rDNA region consisting of a nucleotide sequence beginning at nucleotide 254 and ending at nucleotide 407 of SEQ ID NO:2 as depicted in FIGS. 3A and 3B, and said ITS2 region consisting of a nucleotide sequence beginning at nucleotide 408 and ending at nucleotide 609 of SEQ ID NO: 2 as depicted in FIG. 3B, wherein said contiguous portion is revealed to be identical when a comparison between *P. pachyrhizi* and *P. meibomiae* is made, as depicted in FIG. 3, wherein said twenty to thirty contiguous nucleotides of said probe is conjugated to a detectable label, and wherein said probe specifically hybridizes to said portion of SEQ ID NO:2 or its complement.

27. The probe of claim 25 wherein the detectable label is a chromophore or a fluorophore label.

28. A method of detecting the presence of *P. pachyrhizi* by polymerase chain reaction, said method comprising:

a) providing DNA of *P. pachyrhizi* or a test sample suspected of containing DNA of said *P. pachyrhizi;* b) amplifying a target sequence of DNA of said *P. pachyrhizi* using at least one primer consisting of an eighteen to twenty-four nucleotide contiguous portion of SEQ ID NO:2 or its complement, wherein the primer is a contiguous nucleotide sequence of the ITS1 or the ITS2 region of SEQ ID NO:2, said ITS1 region consisting of a nucleotide sequence beginning at nucleotide 55 and ending at nucleotide 253 of SEQ ID NO: 2 as depicted in FIG. 3A and said ITS2 region consisting of a nucleotide sequence beginning at nucleotide 408 and ending at nucleotide 609 of SEQ ID NO: 2 as depicted in FIG. 3B, wherein said contiguous nucleotide sequence of the primer encompasses at least a single nucleotide difference between *P. pachyrhizi* and *P. meibomiae* at the 3' terminus of the primer when the ITS1 or ITS2 regions are aligned and when a comparison as depicted In FIG. 3 is made between said ITS1 or ITS2 regions, and wherein the primer specifically hybridizes to a region of SEQ ID NO:2 or its complement, and wherein the primer distinguishes *P. pachyrhizi* from *P. meibomiae*; and c) detecting the presence of amplification products of the target sequence of DNA as an indication of the presence of *P. pachyrhizi.*

29. A kit for detecting the presence of *P. pachyrhizi* comprising at least one primer consisting of an eighteen to twenty-four nucleotide contiguous portion of SEQ ID NO:2 or its complement, wherein the primer is a contiguous nucleotide sequence within the ITS1 or the ITS2 region of SEQ ID NO:2, said ITS1 region consisting of a nucleotide sequence beginning at nucleotide 55 and ending at nucleotide 253 of SEQ ID NO: 2 as depicted in FIG. 3A and said ITS2 region consisting of a nucleotide sequence beginning at nucleotide 408 and ending at nucleotide 609 of SEQ ID NO: 2 as depicted in FIG. 3B, wherein said contiguous nucleotide sequence of the primer encompasses at least a single nucleotide difference between *P. pachyrhizi* and *P. meibomiae* at the 3' terminus of the primer when the ITS1 or ITS2 regions are aligned and when a comparison as depicted in FIG. 3 is made between said ITS1 or ITS2 regions, and wherein said primer specifically hybridizes to a region of SEQ ID NO:2 or its complement, and wherein said primer distinguishes *P. pachyrhizi* from *P. meibomiae.*

30. The kit of claim 29 wherein said kit further comprises a probe for the detection of a target sequence of DNA of *P. pachyrhizi* and *P. meibomiae*, wherein said probe consists of about a twenty to thirty nucleotide contiguous portion of the ITS1, the 5.8S rDNA region, or the ITS2 region of SEQ ID NO:2, said ITS1 region consisting of a nucleotide sequence beginning at nucleotide 55 and ending at nucleotide 253 of SEQ ID NO: 2 as depicted in FIG. 3A, said 5.8S rDNA region consisting of a nucleotide sequence beginning at nucleotide 254 and ending at nucleotide 407 of SEQ ID NO:2 as depicted in FIGS. 3A and 3B, and said ITS2 region consisting of a nucleotide sequence beginning at nucleotide 408 and ending at nucleotide 609 of SEQ ID NO: 2 as depicted in FIG. 3B, wherein said contiguous portion is revealed to be identical when a comparison between *P. pachyrhizi* and *P. meibomiae* is made, as depicted in FIG. 3, wherein said twenty to thirty contiguous nucleotides of said probe is conjugated to a detectable label, and wherein said probe specifically hybridizes to said portion of SEQ ID NO:2 or its complement.

31. A kit for detecting the presence of *P. pachyrhizi* and *P. meibomiae* consisting of an oligonucleotide primer consisting of an eighteen to twenty-four nucleotide contiguous portion of SEQ ID NO:2 or of its complement, wherein said eighteen to twenty-four contiguous nucleotides of said primer comprises the contiguous twenty-three nucleotide sequence 5'-GCAGAATTCAGTGAATCATCAAG-3' (SEQ ID NO:9) or at least an eighteen nucleotide contiguous portion of SEQ ID NO:9 for use in real-time PCR.

32. The method of claim 28, wherein step (b) takes place under real-time PCR conditions and at least one primer, which specifically hybridizes to a region of SEQ ID NO:2 or its complement and is capable of distinguishing *P. pachyrhizi* from *P. meibomiae*, encompasses at least a single nucleotide difference between *P. pachyrhizi* and *P. meibomiae* at the 3' terminus of the primer when the ITS1 or ITS2 regions are aligned and when a comparison as depicted in FIG. 3 is made between said ITS1 or ITS2 regions, and specifically hybridizes to a region of SEQ ID NO:2 or its complement, and distinguishes *P. pachyrhizi* from *P. meibomiae*, and is chosen such that the amplification products are detected and quantitated by real-time analysis.

* * * * *

SEQUENCE LISTING

```
<160> NUMBER OF SEQ ID NOS: 25

<210> SEQ ID NO 1
<211> LENGTH: 683
<212> TYPE: DNA
<213> ORGANISM: Phakopsora meibomiae

<400> SEQUENCE: 1

ggaagtaaaa gtcgtaacaa ggtttccgta ggtgaacctg cggaaggatc attaataaaa     60

agcttaaaaa agagtgcact taattgtggc tctaaacaca aaacttttta tataaaccca    120

tttaaactgg ctcagctact tcattgaagt ttttgggcaa atcacagctt tgaaaaaagt    180

tgcaaatcat ctattatatc attgtcattt tttattttat taaataacca aagtcacaaa    240

gaatgtttta taaattttaa aaaatatata taacttttag caatggatct ctaggctctc    300

atatcgatga agaacacagt gaaatgtgat aattaatgtg aattgcagaa ttcagtgaat    360

catcaagttt ttgaacgcac cttgtacctt ttggtattcc aaaaggtaca cctgtttgag    420

tgtcatgaat tattctcaac tctttcttta tttacttaaa gaaaagcatg ttggattttg    480
```

-continued

```
agtgctgctg tgttttaata tagctcactt taaataaata aatatataaa ttcttgtata    540

tatatatggt gtaataataa caaacatttc atcattaatt tatataaagg aatatatata    600

gtattaaatt attattatta aattttaaga cctcaaatca ggtggactac ccactgaact    660

taagcatatc aataagcgga gga                                            683


<210> SEQ ID NO 2
<211> LENGTH: 667
<212> TYPE: DNA
<213> ORGANISM: Phakopsora pachyrhizi

<400> SEQUENCE: 2

ggaagtaaaa gtcgtaacaa ggtttccgta ggtgaacctg cggaaggatc attaataaaa     60

agctaaagag tgcactttat tgtggctcaa aactaaactt tttaataaac ccatttaatt    120

ggctcattga ttgataagat ctttgggcaa tggtagcttt gaaaaaagct gcaacccacc    180

tattaatcat aatctttttt tttttaactc aaagtcaaat agaatgtttt ataaatttaa    240

atatatatat ataactttta acaatggatc tctaggctct catatcgatg aagaacacag    300

tgaaatgtga taattaatgt gaattgcaga attcagtgaa tcatcaagtt tttgaacgca    360

ccttgcacct tttggtattc caaaaggtac acctgtttga gtgtcatgaa atcttctcaa    420

cattatttct ttttttttaaa gggaaattgt tggattttga gtgttgctgt tgcttttttt    480

gcagctcact ttaaataaat aaatatatat aagtttcagt atattttgat gtaataataa    540

aatcatttca tcaaaaaaat aaatatatgt gagatttatt ataacattaa ttgaatgtaa    600

attttttttta agacctcaaa tcaggtgaga ctacccactg aacttaagca tatcaataag    660

cggagga                                                              667


<210> SEQ ID NO 3
<211> LENGTH: 20
<212> TYPE: DNA
<213> ORGANISM: Phakopsora pachyrhizi

<400> SEQUENCE: 3

taagatcttt gggcaatggt                                                 20


<210> SEQ ID NO 4
<211> LENGTH: 22
<212> TYPE: DNA
<213> ORGANISM: Phakopsora pachyrhizi

<400> SEQUENCE: 4

gcaacactca aaatccaaca at                                              22


<210> SEQ ID NO 5
<211> LENGTH: 20
<212> TYPE: DNA
<213> ORGANISM: Phakopsora pachyrhizi

<400> SEQUENCE: 5

cccatttaat tggctcattg                                                 20


<210> SEQ ID NO 6
<211> LENGTH: 20
<212> TYPE: DNA
<213> ORGANISM: Phakopsora pachyrhizi

<400> SEQUENCE: 6

tcaaaatcca acaatttccc                                                 20
```

-continued

<210> SEQ ID NO 7
<211> LENGTH: 20
<212> TYPE: DNA
<213> ORGANISM: Phakopsora meibomiae

<400> SEQUENCE: 7
gaagtttttg ggcaaatcac 20

<210> SEQ ID NO 8
<211> LENGTH: 20
<212> TYPE: DNA
<213> ORGANISM: Phakopsora meibomiae

<400> SEQUENCE: 8
gcactcaaaa tccaacatgc 20

<210> SEQ ID NO 9
<211> LENGTH: 23
<212> TYPE: DNA
<213> ORGANISM: Phakopsora pachyrhizi

<400> SEQUENCE: 9
gcagaattca gtgaatcatc aag 23

<210> SEQ ID NO 10
<211> LENGTH: 22
<212> TYPE: DNA
<213> ORGANISM: Phakopsora pachyrhizi

<400> SEQUENCE: 10
ctcaaacagg tgtacctttt gg 22

<210> SEQ ID NO 11
<211> LENGTH: 27
<212> TYPE: DNA
<213> ORGANISM: Phakopsora pachyrhizi

<400> SEQUENCE: 11
ccaaaaggta cacctgtttg agtgtca 27

<210> SEQ ID NO 12
<211> LENGTH: 24
<212> TYPE: DNA
<213> ORGANISM: Phakopsora pachyrhizi

<400> SEQUENCE: 12
tgaacgcacc ttgcaccttt tggt 24

<210> SEQ ID NO 13
<211> LENGTH: 199
<212> TYPE: DNA
<213> ORGANISM: Phakopsora pachyrhizi

<400> SEQUENCE: 13
ataaaaagct aaagagtgca ctttattgtg gctcaaaact aaacttttta ataaacccat 60
ttaattggct cattgattga taagatcttt gggcaatggt agctttgaaa aaagctgcaa 120
cccacctatt aatcataatc tttttttttt taactcaaag tcaaatagaa tgttttataa 180
atttaaatat atatatata 199

-continued

<210> SEQ ID NO 14
<211> LENGTH: 197
<212> TYPE: DNA
<213> ORGANISM: Phakopsora pachyrhizi

<400> SEQUENCE: 14
ataaaaagct aaagagtgca ctttattgtg gctcaaaact aaacttttta ataaacccat 60
ttaattggct cattgattga taagatcttt gggcaatggt agctttgaaa aaagctgcaa 120
cccacctatt aatcataatc tttttttttt taactcaaag tcaaatagaa tgttttataa 180
atataaatat atatata 197

<210> SEQ ID NO 15
<211> LENGTH: 196
<212> TYPE: DNA
<213> ORGANISM: Phakopsora pachyrhizi

<400> SEQUENCE: 15
ataaaaagct aaagagtgca ctttattgtg gctcaaaact aaacttttta ataaacccat 60
ttaattggct cattgattga taagatcttt gggcaatggt agctttgaaa aaagctgcaa 120
cccacctatt aatcataatc tttttttttt aactcaaagt caaatagaat gttttataaa 180
tttaaatata tatata 196

<210> SEQ ID NO 16
<211> LENGTH: 197
<212> TYPE: DNA
<213> ORGANISM: Phakopsora pachyrhizi

<400> SEQUENCE: 16
ataaaaagct aaagagtgca ctttattgtg gctcaaaact aaacttttta ataaacccat 60
ttaattggct cattgattga taagatcttt gggcaatggt agctttgaaa aaagctgcaa 120
cccacctatt aatcataatc tttttttttt taactcaaag tcaaatagaa tgttttataa 180
atttaaatat atatata 197

<210> SEQ ID NO 17
<211> LENGTH: 200
<212> TYPE: DNA
<213> ORGANISM: Phakopsora pachyrhizi

<400> SEQUENCE: 17
ataaaaagct aaagagtgca ctttattgtg gctcaaaact aaacttttta ataaacccat 60
ttaattggct cattgattga taagatcttt gggcaatggt agctttgaaa aaagctgcaa 120
cccacctatt aatcataatc tttttttttt ttaactcaaa gtcaaataga atgttttata 180
aatataaata tatatatata 200

<210> SEQ ID NO 18
<211> LENGTH: 218
<212> TYPE: DNA
<213> ORGANISM: Phakopsora meibomiae

<400> SEQUENCE: 18
ataaaaagct taaaaaagag tgcacttaat tgtggctcta aacacaaaac tttttatata 60
aacccattta aactggctca gctacttcat tgaagttttt gggcaaatca cagctttgaa 120
aaaagttgca aatcatctat tatatcattg tcatttttta ttttattaaa taaccaaagt 180
cacaaagaat gttttataaa ttttaaaaaa tatatata 218

-continued

<210> SEQ ID NO 19
<211> LENGTH: 203
<212> TYPE: DNA
<213> ORGANISM: Phakopsora pachyrhizi

<400> SEQUENCE: 19
gaaatcttct caacattatt tctttttttt aaagggaaat tgttggattt tgagtgttgc 60
tgttgctttt tttgcagctc actttaaata aataaatata tataagtttc agtatatttt 120
gatgtaataa taaaatcatt tcatcaaaaa aataaatata tgtgagattt attataacat 180
taattgaatg taaatttttt ttt 203

<210> SEQ ID NO 20
<211> LENGTH: 206
<212> TYPE: DNA
<213> ORGANISM: Phakopsora pachyrhizi

<400> SEQUENCE: 20
gaaatcttct caacattatt tctttttttt aaagggaaat tgttggattt tgagtgttgc 60
tgttgctttt ttttgcagct cactttaaat aaataaatat atataagttt cagtatattt 120
tgatgtaata ataaaatcat ttcatcaaaa aaataaatat atgtgagatt tattataaca 180
ttaattgaat gtaaattttt tttttt 206

<210> SEQ ID NO 21
<211> LENGTH: 204
<212> TYPE: DNA
<213> ORGANISM: Phakopsora pachyrhizi

<400> SEQUENCE: 21
gaaatcttct caacattatt tctttttttt aaagggaaat tgttggattt tgagtgttgc 60
tgttgctttt ttttgcagct cactttaaat aaataaatat atataagttt cagtatattt 120
tgatgtaata ataaaatcat ttcatcaaaa aaataaatat atgtgagatt tattataaca 180
ttaattgaat gtaaattttt tttt 204

<210> SEQ ID NO 22
<211> LENGTH: 204
<212> TYPE: DNA
<213> ORGANISM: Phakopsora pachyrhizi

<400> SEQUENCE: 22
gaaatcttct caacattatt tctttttttt aaagggaaat tgttggattt tgagtgttgc 60
tgttgctttt tttgcagctc actttaaata aataaatata tataagtttc agtatatttt 120
gatgtaataa taaaatcatt tcatcaaaaa aataaatata tgtgagattt attataacat 180
taattgaatg taaatttttt tttt 204

<210> SEQ ID NO 23
<211> LENGTH: 199
<212> TYPE: DNA
<213> ORGANISM: Phakopsora pachyrhizi

<400> SEQUENCE: 23
gaaatcttct caacattatt tctttttaaa ggaaattgtt ggattttgag tgttgctgtt 60
gctttttttg cagctcactt taaataaata aatatatata agtttcagta tattttgatg 120
taataataaa atcatttcat caaaaaaata aatatatgtg agatttatta taacattaat 180
tgaatgtaat ttttttttt 199

-continued

```
<210> SEQ ID NO 24
<211> LENGTH: 203
<212> TYPE: DNA
<213> ORGANISM: Phakopsora meibomiae

<400> SEQUENCE: 24

gaattattct caactctttc tttatttact tgaagaaaag catgttggat tttgagtgct     60

gctgtgtttt aatatagctc actttaaata aatagatata taaattcttg tatatatata    120

tggtgtaata ataacaaaca tttcatcatt gatttatata aaggaatata tatagtatta    180

aattattatt attattaaat ttt                                            203


<210> SEQ ID NO 25
<211> LENGTH: 205
<212> TYPE: DNA
<213> ORGANISM: Phakopsora meibomiae

<400> SEQUENCE: 25

gaattattct caactctttc tttatttact tgaagaaaag catgttggat tttgagtgct     60

gctgtgtttt aatatagctc actttaaata aatagatata taaattcttg tatatatata    120

tatggtgtaa taataacaaa catttcatca ttgatttata taaaggaata tatatagtat    180

taaattatta ttattattaa atttt                                          205
```